US008288124B2

(12) United States Patent
Wonderling et al.

(10) Patent No.: US 8,288,124 B2
(45) Date of Patent: *Oct. 16, 2012

(54) CLONING, EXPRESSION AND PURIFICATION OF RECOMBINANT PORCINE INTRINSIC FACTOR FOR USE IN DIAGNOSTIC ASSAY

(75) Inventors: Ramani S. Wonderling, Ivanhoe, IL (US); John F. Uher, Kenosha, WI (US); Thomas P. Leary, Kenosha, WI (US); You Pan, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/275,102

(22) Filed: Nov. 20, 2008

(65) Prior Publication Data

US 2010/0124754 A1    May 20, 2010

(51) Int. Cl.
 C12P 21/06    (2006.01)
(52) U.S. Cl. ..................................................... 435/69.1
(58) Field of Classification Search .................. None
See application file for complete search history.

(56) References Cited

U.S. PATENT DOCUMENTS

| | | | |
|---|---|---|---|
| 3,591,678 | A | 7/1971 | Ellenbogen et al. |
| 4,447,528 | A | 5/1984 | Ellis et al. |
| 4,582,788 | A | 4/1986 | Erlich et al. |
| 4,683,194 | A | 7/1987 | Saiki et al. |
| 4,683,202 | A | 7/1987 | Mullis |
| 4,945,050 | A | 7/1990 | Sanford et al. |
| 5,104,815 | A | 4/1992 | Garner et al. |
| 5,107,065 | A | 4/1992 | Shewmaker et al. |
| 5,227,311 | A | 7/1993 | Kuemmerle et al. |
| 5,231,020 | A | 7/1993 | Jorgensen et al. |
| 5,350,674 | A | 9/1994 | Boenisch et al. |
| 5,459,242 | A | 10/1995 | Kuemmerle |
| 5,795,784 | A | 8/1998 | Arnquist et al. |
| 5,912,120 | A | 6/1999 | Goldstein et al. |
| 6,183,723 | B1 | 2/2001 | Seetharam et al. |
| 6,746,668 | B2 * | 6/2004 | Ashkenazi .................... 424/85.1 |
| 2003/0036629 | A1 * | 2/2003 | Foster et al. .................... 530/344 |
| 2006/0177872 | A1 | 8/2006 | Wonderling et al. |

FOREIGN PATENT DOCUMENTS

| | | |
|---|---|---|
| EP | 0 050 424 | 4/1982 |
| EP | 0 084 796 | 8/1983 |
| EP | 0 201 184 | 12/1986 |
| EP | 0 237 362 | 9/1987 |
| EP | 0 258 017 | 3/1988 |
| JP | 05015375 | 1/1993 |
| JP | 05049478 | 3/1993 |
| JP | 06153935 | 6/1994 |
| JP | 06205673 | 7/1994 |
| WO | 92/18539 | 10/1992 |
| WO | WO2006086204 A1 | 8/2006 |

OTHER PUBLICATIONS

Ausubel, et al., Techniques in Biochemistry and Molecular BiologyHybridization with Nucleic Acid Probes, "Overview of principles of hybridization and the strategy of nucleic acid assays", Short Protocols in Molecular Biology, 19-78, (1993).

Azzazy H., and Highsmith W.E.,Phage display technology: clinical applications and recent innovations, Clin. Biochem. 35:425-445 (2002).

De Almeida, et al., Transgenic expression of two marker genes under the control of an *Arabidopsis rbcS* promoter: Sequences encoding the Rubisco transit peptide increase expression levels., Mol. Gen. Genetics, 218: 78-86 (1989).

Gavilondo J.V., and Larrick J.W., Bio Techniques, 29:128-145 (2002).

Geige R., et al., Crystallization of Nucleic Acids and Proteins, a Practical Approach, $2^{nd}$ ea. pp. 20 1-16, Oxford University Press, New York, NY (1999).

Higgins, et al., CABIOS, 5L151-153 (1989).

Holliger, P., et al., Proc. Natl. Acad. Sci. USA 90: 6444-6448 (1993).

Hoogenboom H.R., TIB Tech. 15: 62-70 (1997).

Hoogenboom H., et al., Today, 21: 371-378 (2000).

Huston et al. Proc. Natl. Acad. Sci. USA; 85: 5879-5883 (1988).

Ingelbrecht, et al., Different 3' End Regions Strongly Influence the Level of Gene Expression in Plant Cells, The Plant Cell 1:671-680 (1989).

Ishida, et al., High efficiency transformation of maize (*Zea mays* L.) mediated by *Agrobacterium tumefaciens*, Nature Biotechnology, vol. 14: 745-750 (Jun. 1996).

Jones, et al., High level expression of introduced chimaeric genes in regenerated transformed plants, The EMBO Journal, vol. 4, No. 10, 2411-2418 (1985).

Kipriyanov, S.M. et al., Human Antiobodies and Hybridomas, 6: 93-101 (1995).

Kipriyanov, S.M. et al., Molecular Immunology, V31: 1047-1058, (1994).

Klein, et al., High-velocity microprojectiles for delivering nucleic acids into living cells, Nature (London) 327:70-73 (1987).

Kohler and Milstein, hybridoma methodology, Nature, 256:495-497 (1975).

Kontermann and Dubel eds., Antibody Engineering, Springer-Verlag. New York, 790 pp. (2001).

Little M., et al., Immunology Today, 21: 364-370 (2000).

Mullis, et al., Specific Enzymatic Amplification of DNA In Vitro: The Polymerase Chain Reaction, Cold Spring Harbor Symposia on Quantitative Biology, vol. LL: 263-273 (1986).

Needleman & Wunsch, J.Mol. Biol., V48: 443-453 (1970).

Polijak, R. J. et. al., Structure 2: 1121-1123 (1994).

(Continued)

*Primary Examiner* — Albert Navarro
(74) *Attorney, Agent, or Firm* — Cheryl L. Becker

(57) ABSTRACT

The present invention relates to a new method of producing functionally active recombinant porcine Intrinsic Factor as well as the protein (i.e., porcine Intrinsic Factor) produced thereby. In particular, the vector comprising the DNA encoding the protein is introduced into a Chinese Hamster Ovary (CHO) host cell under conditions sufficient for optimal expression of functional protein. The expressed protein may then be subjected to three methods ultimately resulting in a protein having at least 97% purity.

8 Claims, 3 Drawing Sheets

OTHER PUBLICATIONS

Sambrook, et al., Molecular Cloning: A Laboratory Manual, Table of Contents, Second Edition (1989).
U.S. Appl. No. 11/052,128, filed Feb. 7, 2005, Wonderling, et al.
Pearson & Lipman, Proc. Natl. Acad. Sci. (USA), V85: 2444 (1988).
Smith & Waterman, Appl. Math., V2: 482 (1981).
Taylor, L.D., et al Nucl. Acides Res. 20: 6287-6295 (1992).
Turner, et al., The Potential Exploitation of Plant Viral Translational Enhancers in Biotechnology for Increased Gene Expression, *Molecular Biotechnology*, 3:225-236 (1995).
Abbott Laboratories, ARCHITECT™ System B12 (Dec. 1998) Abbott Park, Illinois.
Abbott Laboratories, Abbott AxSym® System B12 (Feb. 1999) Abbott Park, Illinois.
Abbott Laboratories, IM® X System B12 (1999) Abbott Park, Illinois.
Altschuel S.F., et al., "Gapped BLAST and PSI-BLAST: A New Generation of Protein Database Search Programs," Nucleic Acids Research, 1997, 25 (17), pp. 3389-3402.
Bird R.E., et al., "Single-Chain Antigen Binding Proteins," Science, 1988, vol. 242 (4877), pp. 423-426.
Brutlag, D., "Computational Molecular Biology Multiple Sequence Alignment," Departments of Biochemistry and Medicine Standford University School of Medicine, 2007, pp. 1-54.
Kellerman S.A., et al., "Antibody Discovery: The Use of Transgenic Mice to Generate Human Monoclonal Antibodies for Therapeutics," Current Opinion in Biotechnology, 2002, vol. 13 (6), pp. 593-597.
Ward E.S., et al., "Binding Activites of a Repertoire of Single Immunoglobulin Variable Domains Secreted from *Escherichia coli*," Nature, 1989, vol. 341 (6242), pp. 544-546.
International Search Report for Application No. PCT/US2009/065082, mailed on Feb. 2, 2010, 4 pages.

\* cited by examiner

Gel 2:

| Lane | Sample | Volume |
|---|---|---|
| 1 | Pre-stained BRMWM | 10 μl |
| 2 | Native IF | 10 μl |
| 3 | Bulk Clones 11-13-06 Concentrated | 10 μl |
| 4 | Clone #4 Concentrated | 10 μl |
| 5 | Clone #8 Concentrated | 10 μl |
| 6 | Clone #10 Concentrated | 10 μl |
| 7 | Clone #13 Concentrated | 10 μl |
| 8 | Clone #17 Concentrated | 10 μl |
| 9 | Clone #21 Concentrated | 10 μl |
| 10 | Blank | 10 μl |

G000981-176 Conjugate Blot #2

Conjugate Blot

| Lane | Sample | Volume |
|---|---|---|
| 1 | Pre-stained BRMWM | 10 μl |
| 2 | Native IF | 20 μl |
| 3 | Blank | 10 μl |
| 4 | Bulk + B12 | 20 μl |
| 5 | Bulk + B12 | 20 μl |
| 6 | Clone #13 + B12 | 20 μl |
| 7 | Clone #13 − B12 | 20 μl |
| 8 | Clone #21 + B12 | 20 μl |
| 9 | Clone #21 − B12 | 20 μl |
| 10 | Blank | 10 μl |

Eceo981-179 Conj Blot

Architect Run:
The following samples were read on the Architect

| Samples | Sample Abbreviations for Architect | Results from Architect |
|---|---|---|
| Calibrator A | CalA | N/A* |
| Calibrator B | CalB | 173880 |
| Calibrator C | CalC | 120499 |
| Calibrator D | CalD | 79053 |
| Calibrator E | CalE | 47389 |
| Calibrator F | CalF | 26307 |
| Low Control | LCtr | 51593, 51984 |
| Medium Control | MCtr | 43053, 42281 |
| High Control | HCtr | 128913, 130261 |
| B12 Free Media | Med | 203192 |
| Bulk Supernatant (Date Unknown) | BNone | 90844 |
| Bulk Supernatant (12/12/06) | B1212 | 80021 |
| Bulk Supernatant (12/21/06) | B1221 | 54299 |
| Bulk Supernatant (1/2/07) | B0102 | 80884 |
| Clone 13 Supernatant (Date Unknown) | C13None | 125555 |
| Clone 13 Supernatant (12/12/06) | C131212 | 116558 |
| Clone 13 Supernatant (12/21/06) | C131221 | 155999 |
| Clone 13 Supernatant (1/2/07) | C130102 | 130689 |
| Clone 21 Supernatant (Date Unknown) | C21None | 77947 |
| Clone 21 Supernatant (12/12/06) | C211212 | 40201 |
| Clone 21 Supernatant (12/21/06) | C211221 | 24815 |
| Clone 21 Supernatant (1/2/07) | C210102 | 32174 |
| Clone 21 (12/21/06) Supernatant after incubation with B12 Agarose | C21Sup | 5591 |
| Clone 21 (12/21/06) Purified Supernatant using B12 Agarose | C21Pur | 195064 |
| CD CHO Media With B12 | MedB12 | 775 |
| Clone #21 Supernatant With B12 | C21B12 | 750 |

* Insufficient Cal A available to perform run so B12 Microparticle dilute utilized. Normal background result is approximately 200,000.

FIG.3

SEQUENCE LISTING

<160> NUMBER OF SEQ ID NOS: 23

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccctctacct cctgagcctt ctctgggct                                        29

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctgtgtgaaa ttggctgtga tgtgc                                            25

<210> SEQ ID NO 3
<211> LENGTH: 1234
<212> TYPE: DNA
<213> ORGANISM: Sus sp.

<400> SEQUENCE: 3

```
cctctacctc ctgagccttc tctgggctgt ggccggaacc agcacccaga cccgaagctc      60
atgctctgtt ccctctgcag agcagccctt ggttaatggc atccaggtgc tcatggagca     120
gtccgtgacc agctcggcct tcccaaaccc cagcatcctg attgccatga acctggccgg     180
agcctacaac acagaggccc aggagctcct gacttacaag ctcatggcta ccaacacctc     240
cgacctgacc acaggtcagc tcgccctcac catcatggca ctcacctcct cctgccgaga     300
ccctgggaac agaatagcca ttctacaggg gcaaatggag aactgggcac ctccaagcct     360
tgatacccat gcttcaacct tctacgagcc aagtctgggg atcctgacgc tgtgccagaa     420
taacccggag aagaccttac cgctagcagc ccgttttgcc aagaccctgc tggccaattc     480
ctctcccttc aacatggaca caggagcaat ggcaaccttg ccctgacct gtatgtacaa     540
caagatcccc gtaggctcag aggaagggta cagagccctg ttcagtcagg tactgaggaa     600
tactgtggag aatatcagca tgaggatcca agacaacgga atcattggaa acatctatag     660
cactggcctc gccatgcagg ctctctctgt gacacctgag caacctaaca aggagtggga     720
ctgccagaag accatggata ctgtacttac tgagattaag gaggggaaat ccacaaccc      780
catggccatt gcccaaatcc tcccttccct gaaaggcaag acctatctag atgtgcccca     840
tgtgtcttgc agccctggtc atgaggtgcc accaactcta cccaaccacc ccagccctgt     900
tcccacccca gcacccaaca tcaccgtcat atacaccata ataaccagc tgaggggcgt      960
ggagctgctc ttcaatgaaa ccatcagtgt tagtgtgaaa agaggatccg tgctacttat    1020
tgtcctggag gaggcacagc gcaaaaaccc caagttcaaa tttgaaacga caatgacgtc    1080
ctggggaccg gtggtctctt ctattaacaa tatcgctgaa aatgtcaacc acaggacgta    1140
ctggcagttt ctgagtggcc aaacgccctt aaacgaagga gttgcggact atataccctt    1200
caaccacgag cacatcacag ccaatttcac acag                                 1234
```

<210> SEQ ID NO 4
<211> LENGTH: 1234
<212> TYPE: DNA
<213> ORGANISM: Sus sp.

<400> SEQUENCE: 4

```
ctgtgtgaaa ttggctgtga tgtgctcgtg gttgaagggt atatagtccg caactccttc      60
gtttaagggc gtttggccac tcagaaactg ccagtacgtc ctgtggttga catttcagc     120
gatattgtta atagaagaga ccaccggtcc ccaggacgtc attgtcgttt caaatttgaa     180
cttggggttt ttgcgctgtg cctcctccag gacaataagt agcacggatc ctcttttcac     240
actaacactg atggtttcat tgaagagcag ctccacgccc ctcagctggt tatttatggt     300
gtatatgacg gtgatgttgg gtgctggggt gggaacaggg ctggggtggt tgggtagagt     360
tggtggcacc tcatgaccag ggctgcaaga cacatgggc acatctagat aggtcttgcc     420
tttcagggaa gggaggattt gggcaatggc catgggggttg tggaatttcc cctccttaat     480
ctcagtaagt acagtatcca tggtcttctg gcagtcccac tccttgttag gttgctcagg     540
tgtcacagag agagcctgca tggcgaggcc agtgctatag atgtttccaa tgattccgtt     600
gtcttggatc ctcatgctga tattctccac agtattcctc agtacctgac tgaacagggc     660
tctgtaccct tcctctgagc ctacggggat cttgttgtac atacaggtca gggccaaggt     720
tgccattgct cctgtgtcca tgttgaaggg agaggaattg ccagcaggg tcttggcaaa     780
acgggctgct agcggtaagg tcttctccgg gttattctgg cacagcgtca ggatccccag     840
```

```
acttggctcg tagaaggttg aagcatgggt atcaaggctt ggaggtgccc agttctccat    900
ttgcccctgt agaatggcta ttctgttccc agggtctcgg caggaggagg tgagtgccat    960
gatggtgagg gcgagctgac ctgtggtcag gtcggaggtg ttggtagcca tgagcttgta   1020
agtcaggagc tcctgggcct ctgtgttgta ggctccggcc aggttcatgg caatcaggat   1080
gctggggttt gggaaggccg agctggtcac ggactgctcc atgagcacct ggatgccatt   1140
aaccaagggc tgctctgcag agggaacaga gcatgagctt cgggtctggg tgctggttcc   1200
ggccacagcc cagagaaggc tcaggaggta gagg                               1234
```

<210> SEQ ID NO 5
<211> LENGTH: 411
<212> TYPE: PRT
<213> ORGANISM: Sus sp.

<400> SEQUENCE: 5

```
Leu Tyr Leu Leu Ser Leu Leu Trp Ala Val Ala Gly Thr Ser Thr Gln
1               5                   10                  15

Thr Arg Ser Ser Cys Ser Val Pro Ser Ala Glu Gln Pro Leu Val Asn
            20                  25                  30

Gly Ile Gln Val Leu Met Glu Gln Ser Val Thr Ser Ser Ala Phe Pro
        35                  40                  45

Asn Pro Ser Ile Leu Ile Ala Met Asn Leu Ala Gly Ala Tyr Asn Thr
    50                  55                  60

Glu Ala Gln Glu Leu Leu Thr Tyr Lys Leu Met Ala Thr Asn Thr Ser
65                  70                  75                  80

Asp Leu Thr Thr Gly Gln Leu Ala Leu Thr Ile Met Ala Leu Thr Ser
                85                  90                  95

Ser Cys Arg Asp Pro Gly Asn Arg Ile Ala Ile Leu Gln Gly Gln Met
            100                 105                 110

Glu Asn Trp Ala Pro Pro Ser Leu Asp Thr His Ala Ser Thr Phe Tyr
        115                 120                 125

Glu Pro Ser Leu Gly Ile Leu Thr Leu Cys Gln Asn Asn Pro Glu Lys
    130                 135                 140

Thr Leu Pro Leu Ala Ala Arg Phe Ala Lys Thr Leu Leu Ala Asn Ser
145                 150                 155                 160

Ser Pro Phe Asn Met Asp Thr Gly Ala Met Ala Thr Leu Ala Leu Thr
                165                 170                 175

Cys Met Tyr Asn Lys Ile Pro Val Gly Ser Glu Glu Gly Tyr Arg Ala
            180                 185                 190

Leu Phe Ser Gln Val Leu Arg Asn Thr Val Glu Asn Ile Ser Met Arg
        195                 200                 205

Ile Gln Asp Asn Gly Ile Ile Gly Asn Ile Tyr Ser Thr Gly Leu Ala
    210                 215                 220

Met Gln Ala Leu Ser Val Thr Pro Glu Gln Pro Asn Lys Glu Trp Asp
225                 230                 235                 240

Cys Gln Lys Thr Met Asp Thr Val Leu Thr Glu Ile Lys Glu Gly Lys
                245                 250                 255

Phe His Asn Pro Met Ala Ile Ala Gln Ile Leu Pro Ser Leu Lys Gly
            260                 265                 270

Lys Thr Tyr Leu Asp Val Pro His Val Ser Cys Ser Pro Gly His Glu
        275                 280                 285

Val Pro Pro Thr Leu Pro Asn His Pro Ser Val Pro Thr Pro Ala
    290                 295                 300

Pro Asn Ile Thr Val Ile Tyr Thr Ile Asn Asn Gln Leu Arg Gly Val
```

```
                305                 310                 315                 320
Glu Leu Leu Phe Asn Glu Thr Ile Ser Val Ser Val Lys Arg Gly Ser
                    325                 330                 335
Val Leu Leu Ile Val Leu Glu Glu Ala Gln Arg Lys Asn Pro Lys Phe
                340                 345                 350
Lys Phe Glu Thr Thr Met Thr Ser Trp Gly Pro Val Val Ser Ser Ile
            355                 360                 365
Asn Asn Ile Ala Glu Asn Val Asn His Arg Thr Tyr Trp Gln Phe Leu
                370                 375                 380
Ser Gly Gln Thr Pro Leu Asn Glu Gly Val Ala Asp Tyr Ile Pro Phe
385                 390                 395                 400
Asn His Glu His Ile Thr Ala Asn Phe Thr Gln
                405                 410

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
atggcctggt tgccctcta cctcctgagc cttctc                                    36

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gatggtgatg atggtactgt gtgaaattgg ctgtgatg                                 38

<210> SEQ ID NO 8
<211> LENGTH: 1264
<212> TYPE: DNA
<213> ORGANISM: Sus sp.

<400> SEQUENCE: 8
atggcctggt tgccctcta cctcctgagc cttctctggg ctgtggccgg aaccagcacc           60
cagacccgaa gctcatgctc tgttccctct gcagagcagc ccttggttaa tggcatccag         120
gtgctcatgg agcagtccgt gaccagctcg gccttcccaa accccagcat cctgattgcc         180
atgaacctgg ccggagccta caacacagag gcccaggagc tcctgactta caagctcatg         240
gctaccaaca cctccgacct gaccacaggt cagctcgccc tcaccatcat ggcactcacc         300
tcctcctgcc gagaccctgg gaacagaata gccattctac aggggcaaat ggagaactgg         360
gcacctccaa gccttgatac ccatgcttca accttctacg agccaagtct ggggatcctg         420
acgctgtgcc agaataaccc ggagaagacc ttaccgctag cagcccgttt tgccaagacc         480
ctgctggcca attcctctcc cttcaacatg gacacaggag caatggcaac cttggccctg         540
acctgtatgt acaacaagat ccccgtaggc tcagaggaag gtacagagc  cctgttcagt         600 caggtactga ggaatactgt ggagaatatc agcatgagga tccaagacaa cggaatcatt         660
ggaaacatct atagcactgg cctcgccatg caggctctct ctgtgacacc tgagcaacct         720
aacaaggagt gggactgcca gaagaccatg gatactgtac ttactgagat taaggagggg         780
```

-continued

| | |
|---|---|
| aaattccaca accccatggc cattgcccaa atcctccctt ccctgaaagg caagacctat | 840 |
| ctagatgtgc cccatgtgtc ttgcagccct ggtcatgagg tgccaccaac tctacccaac | 900 |
| caccccagcc ctgttcccac cccagcaccc aacatcaccg tcatatacac cataaataac | 960 |
| cagctgaggg gcgtggagct gctcttcaat gaaaccatca gtgttagtgt gaaaagagga | 1020 |
| tccgtgctac ttattgtcct ggaggaggca cagcgcaaaa accccaagtt caaatttgaa | 1080 |
| acgacaatga cgtcctgggg accggtggtc tcttctatta acaatatcgc tgaaaatgtc | 1140 |
| aaccacagga cgtactggca gtttctgagt ggccaaacgc ccttaaacga aggagttgcg | 1200 |
| gactatatac ccttcaacca cgagcacatc acagccaatt tcacacagta ccatcatcac | 1260 |
| catc | 1264 |

<210> SEQ ID NO 9
<211> LENGTH: 1264
<212> TYPE: DNA
<213> ORGANISM: Sus sp.

<400> SEQUENCE: 9

| | |
|---|---|
| gatggtgatg atggtactgt gtgaaattgg ctgtgatgtg ctcgtggttg aagggtatat | 60 |
| agtccgcaac tccttcgttt aagggcgttt ggccactcag aaactgccag tacgtcctgt | 120 |
| ggttgacatt ttcagcgata ttgttaatag aagagaccac cggtccccag gacgtcattg | 180 |
| tcgtttcaaa tttgaacttg gggttttttgc gctgtgcctc ctccaggaca ataagtagca | 240 |
| cggatcctct tttcacacta acactgatgg tttcattgaa gagcagctcc acgcccctca | 300 |
| gctggttatt tatggtgtat atgacggtga tgttgggtgc tggggtggga acagggctgg | 360 |
| ggtggttggg tagagttggt ggcacctcat gaccagggct gcaagacaca tggggcacat | 420 |
| ctagataggt cttgcctttc agggaaggga ggatttgggc aatggccatg gggttgtgga | 480 |
| atttcccctc cttaatctca gtaagtacag tatccatggt cttctggcag tcccactcct | 540 |
| tgttaggttg ctcaggtgtc acagagagag cctgcatggc gaggccagtg ctatagatgt | 600 |
| ttccaatgat tccgttgtct tggatcctca tgctgatatt ctccacagta ttcctcagta | 660 |
| cctgactgaa cagggctctg taccccttcct ctgagcctac ggggatcttg ttgtacatac | 720 |
| aggtcagggc caaggttgcc attgctcctg tgtccatgtt gaagggagag gaattggcca | 780 |
| gcagggtctt ggcaaaacgg gctgctagcg gtaaggtctt ctccgggtta ttctggcaca | 840 |
| gcgtcaggat ccccagactt ggctcgtaga aggttgaagc atgggtatca aggcttggag | 900 |
| gtgcccagtt ctccatttgc ccctgtagaa tggctattct gttcccaggg tctcggcagg | 960 |
| aggaggtgag tgccatgatg gtgagggcga gctgacctgt ggtcaggtcg gaggtgttgg | 1020 |
| tagccatgag cttgtaagtc aggagctcct gggcctctgt gttgtaggct ccggccaggt | 1080 |
| tcatggcaat caggatgctg gggtttggga aggccgagct ggtcacggac tgctccatga | 1140 |
| gcacctggat gccattaacc aagggctgct ctgcagaggg aacagagcat gagcttcggg | 1200 |
| tctgggtgct ggttccggcc acagcccaga gaaggctcag gaggtagagg gcaaaccagg | 1260 |
| ccat | 1264 |

<210> SEQ ID NO 10
<211> LENGTH: 421
<212> TYPE: PRT
<213> ORGANISM: Sus sp.

<400> SEQUENCE: 10

Met Ala Trp Phe Ala Leu Tyr Leu Leu Ser Leu Leu Trp Ala Val Ala
1               5                   10                  15

```
Gly Thr Ser Thr Gln Thr Arg Ser Ser Cys Ser Val Pro Ser Ala Glu
            20                  25                  30

Gln Pro Leu Val Asn Gly Ile Gln Val Leu Met Glu Gln Ser Val Thr
            35                  40                  45

Ser Ser Ala Phe Pro Asn Pro Ser Ile Leu Ile Ala Met Asn Leu Ala
 50                  55                  60

Gly Ala Tyr Asn Thr Glu Ala Gln Glu Leu Leu Thr Tyr Lys Leu Met
 65                  70                  75                  80

Ala Thr Asn Thr Ser Asp Leu Thr Thr Gly Gln Leu Ala Leu Thr Ile
             85                  90                  95

Met Ala Leu Thr Ser Ser Cys Arg Asp Pro Gly Asn Arg Ile Ala Ile
            100                 105                 110

Leu Gln Gly Gln Met Glu Asn Trp Ala Pro Pro Ser Leu Asp Thr His
            115                 120                 125

Ala Ser Thr Phe Tyr Glu Pro Ser Leu Gly Ile Leu Thr Leu Cys Gln
            130                 135                 140

Asn Asn Pro Glu Lys Thr Leu Pro Leu Ala Ala Arg Phe Ala Lys Thr
145                 150                 155                 160

Leu Leu Ala Asn Ser Ser Pro Phe Asn Met Asp Thr Gly Ala Met Ala
            165                 170                 175

Thr Leu Ala Leu Thr Cys Met Tyr Asn Lys Ile Pro Val Gly Ser Glu
            180                 185                 190

Glu Gly Tyr Arg Ala Leu Phe Ser Gln Val Leu Arg Asn Thr Val Glu
            195                 200                 205

Asn Ile Ser Met Arg Ile Gln Asp Asn Gly Ile Ile Gly Asn Ile Tyr
210                 215                 220

Ser Thr Gly Leu Ala Met Gln Ala Leu Ser Val Thr Pro Glu Gln Pro
225                 230                 235                 240

Asn Lys Glu Trp Asp Cys Gln Lys Thr Met Asp Thr Val Leu Thr Glu
            245                 250                 255

Ile Lys Glu Gly Lys Phe His Asn Pro Met Ala Ile Ala Gln Ile Leu
            260                 265                 270

Pro Ser Leu Lys Gly Lys Thr Tyr Leu Asp Val Pro His Val Ser Cys
            275                 280                 285

Ser Pro Gly His Glu Val Pro Pro Thr Leu Pro Asn His Pro Ser Pro
            290                 295                 300

Val Pro Thr Pro Ala Pro Asn Ile Thr Val Ile Tyr Thr Ile Asn Asn
305                 310                 315                 320

Gln Leu Arg Gly Val Glu Leu Leu Phe Asn Glu Thr Ile Ser Val Ser
            325                 330                 335

Val Lys Arg Gly Ser Val Leu Leu Ile Val Leu Glu Glu Ala Gln Arg
            340                 345                 350

Lys Asn Pro Lys Phe Lys Phe Glu Thr Met Thr Ser Trp Gly Pro
            355                 360                 365

Val Val Ser Ser Ile Asn Asn Ile Ala Glu Asn Val Asn His Arg Thr
            370                 375                 380

Tyr Trp Gln Phe Leu Ser Gly Gln Thr Pro Leu Asn Glu Gly Val Ala
385                 390                 395                 400

Asp Tyr Ile Pro Phe Asn His Glu His Ile Thr Ala Asn Phe Thr Gln
            405                 410                 415

Tyr His His His His
            420
```

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
cgactaagct tccaccatgg cctggtttgc cctcta        36

<210> SEQ ID NO 12
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
aatcctcgag ttaatggtga tggtgatgat ggtactgtgt g        41

<210> SEQ ID NO 13
<211> LENGTH: 1298
<212> TYPE: DNA
<213> ORGANISM: Sus sp.

<400> SEQUENCE: 13
cgactaagct tccaccatgg cctggtttgc cctctacctc ctgagccttc tctgggctgt      60
ggccggaacc agcacccaga cccgaagctc atgctctgtt ccctctgcag agcagccctt     120
ggttaatggc atccaggtgc tcatggagca gtccgtgacc agctcggcct tcccaaaccc     180
cagcatcctg attgccatga acctggccgg agcctacaac acagaggccc aggagctcct     240
gacttacaag ctcatggcta ccaacaccct cgacctgacc acaggtcagc tcgccctcac     300
catcatggca ctcacctcct cctgccgaga ccctgggaac agaatagcca ttctacaggg     360
gcaaatggag aactgggcac tccaagcct tgatacccat gcttcaacct tctacgagcc     420
aagtctgggg atcctgacgc tgtgccagaa taacccggag aagaccttac cgctagcagc     480
ccgttttgcc aagaccctgc tggccaattc ctctcccttc aacatggaca caggagcaat     540
ggcaaccttg gccctgacct gtatgtacaa caagatcccc gtaggctcag aggaagggta     600
cagagccctg ttcagtcagg tactgaggaa tactgtggag aatatcagca tgaggatcca     660
agacaacgga atcattggaa acatctatag cactggcctc gccatgcagg ctctctctgt     720
gacacctgag caacctaaca aggagtggga ctgccagaag accatggata ctgtacttac     780
tgagattaag gagggaaat tccacaaccc catggccatt gcccaaatcc tcccttccct     840
gaaaggcaag acctatctag atgtgcccca tgtgtcttgc agccctggtc atgaggtgcc     900
accaactcta cccaaccacc ccagcccgt tcccacccca gcaccaaca tcaccgtcat      960
atacaccata aataaccagc tgaggggcgt ggagctgctc ttcaatgaaa ccatcagtgt    1020
tagtgtgaaa agaggatccg tgctacttat tgtcctggag gaggcacagc gcaaaaaccc    1080
caagttcaaa tttgaaacga caatgacgtc ctggggaccg gtggtctctt ctattaacaa    1140
tatcgctgaa aatgtcaacc acaggacgta ctggcagttt ctgagtggcc aaacgccctt    1200
aaaacgaagga gttgcggact atatacccct caaccacgag cacatcacag ccaatttcac    1260
acagtaccat catcaccatc accattaact cgaggatt      1298

<210> SEQ ID NO 14
<211> LENGTH: 1298

```
<212> TYPE: DNA
<213> ORGANISM: Sus sp.

<400> SEQUENCE: 14
aatcctcgag ttaatggtga tggtgatgat ggtactgtgt gaaattggct gtgatgtgct      60
cgtggttgaa gggtatatag tccgcaactc cttcgtttaa gggcgtttgg ccactcagaa     120
actgccagta cgtcctgtgg ttgacatttt cagcgatatt gttaatagaa gagaccaccg     180
gtccccagga cgtcattgtc gtttcaaatt tgaacttggg gttttgcgc  tgtgcctcct     240
ccaggacaat aagtagcacg gatcctcttt tcacactaac actgatggtt tcattgaaga     300
gcagctccac gccctcagc tggttattta tggtgtatat gacggtgatg ttgggtgctg      360
gggtgggaac agggctgggg tggttgggta gagttggtgg cacctcatga ccagggctgc     420
aagacacatg gggcacatct agataggtct tgcctttcag ggaagggagg atttgggcaa     480
tggccatggg gttgtggaat ttcccctcct taatctcagt aagtacagta tccatggtct     540
tctggcagtc ccactccttg ttaggttgct caggtgtcac agagagagcc tgcatggcga     600
ggccagtgct atagatgttt ccaatgattc cgttgtcttg atcctcatg  ctgatattct     660
ccacagtatt cctcagtacc tgactgaaca gggctctgta cccttcctct gagcctacgg     720
ggatcttgtt gtacatacag gtcagggcca aggttgccat tgctcctgtg tccatgttga     780
agggagagga attggccagc agggtcttgg caaaacgggc tgctagcggt aaggtcttct     840
ccgggttatt ctggcacagc gtcaggatcc ccagacttgg ctcgtagaag gttgaagcat     900
gggtatcaag gcttggaggt gcccagttct ccatttgccc ctgtagaatg ctattctgt      960
tcccagggtc tcggcaggag gaggtgagtg ccatgatggt gagggcgagc tgacctgtgg    1020
tcaggtcgga ggtgttggta gccatgagct tgtaagtcag gagctcctgg gcctctgtgt    1080
tgtaggctcc ggccaggttc atggcaatca ggatgctggg gtttgggaag gccgagctgg    1140
tcacggactg ctccatgagc acctggatgc cattaaccaa gggctgctct gcagagggaa    1200
cagagcatga gcttcgggtc tgggtgctgg ttccggccac agcccagaga aggctcagga    1260
ggtagagggc aaaccaggcc atggtggaag cttagtcg                             1298

<210> SEQ ID NO 15
<211> LENGTH: 423
<212> TYPE: PRT
<213> ORGANISM: Sus sp.

<400> SEQUENCE: 15

Met Ala Trp Phe Ala Leu Tyr Leu Leu Ser Leu Leu Trp Ala Val Ala
1               5                   10                  15

Gly Thr Ser Thr Gln Thr Arg Ser Ser Cys Ser Val Pro Ser Ala Glu
            20                  25                  30

Gln Pro Leu Val Asn Gly Ile Gln Val Leu Met Glu Gln Ser Val Thr
        35                  40                  45

Ser Ser Ala Phe Pro Asn Pro Ser Ile Leu Ile Ala Met Asn Leu Ala
    50                  55                  60

Gly Ala Tyr Asn Thr Glu Ala Gln Glu Leu Leu Thr Tyr Lys Leu Met
65                  70                  75                  80

Ala Thr Asn Thr Ser Asp Leu Thr Thr Gly Gln Leu Ala Leu Thr Ile
                85                  90                  95

Met Ala Leu Thr Ser Ser Cys Arg Asp Pro Gly Asn Arg Ile Ala Ile
            100                 105                 110

Leu Gln Gly Gln Met Glu Asn Trp Ala Pro Pro Ser Leu Asp Thr His
        115                 120                 125
```

Ala Ser Thr Phe Tyr Glu Pro Ser Leu Gly Ile Leu Thr Leu Cys Gln
130                 135                 140

Asn Asn Pro Glu Lys Thr Leu Pro Leu Ala Ala Arg Phe Ala Lys Thr
145                 150                 155                 160

Leu Leu Ala Asn Ser Ser Pro Phe Asn Met Asp Thr Gly Ala Met Ala
            165                 170                 175

Thr Leu Ala Leu Thr Cys Met Tyr Asn Lys Ile Pro Val Gly Ser Glu
            180                 185                 190

Glu Gly Tyr Arg Ala Leu Phe Ser Gln Val Leu Arg Asn Thr Val Glu
        195                 200                 205

Asn Ile Ser Met Arg Ile Gln Asp Asn Gly Ile Ile Gly Asn Ile Tyr
210                 215                 220

Ser Thr Gly Leu Ala Met Gln Ala Leu Ser Val Thr Pro Glu Gln Pro
225                 230                 235                 240

Asn Lys Glu Trp Asp Cys Gln Lys Thr Met Asp Thr Val Leu Thr Glu
            245                 250                 255

Ile Lys Glu Gly Lys Phe His Asn Pro Met Ala Ile Ala Gln Ile Leu
            260                 265                 270

Pro Ser Leu Lys Gly Lys Thr Tyr Leu Asp Val Pro His Val Ser Cys
        275                 280                 285

Ser Pro Gly His Glu Val Pro Pro Thr Leu Pro Asn His Pro Ser Pro
290                 295                 300

Val Pro Thr Pro Ala Pro Asn Ile Thr Val Ile Tyr Thr Ile Asn Asn
305                 310                 315                 320

Gln Leu Arg Gly Val Glu Leu Leu Phe Asn Glu Thr Ile Ser Val Ser
            325                 330                 335

Val Lys Arg Gly Ser Val Leu Leu Ile Val Leu Glu Glu Ala Gln Arg
            340                 345                 350

Lys Asn Pro Lys Phe Lys Phe Glu Thr Thr Met Thr Ser Trp Gly Pro
        355                 360                 365

Val Val Ser Ser Ile Asn Asn Ile Ala Glu Asn Val Asn His Arg Thr
370                 375                 380

Tyr Trp Gln Phe Leu Ser Gly Gln Thr Pro Leu Asn Glu Gly Val Ala
385                 390                 395                 400

Asp Tyr Ile Pro Phe Asn His Glu His Ile Thr Ala Asn Phe Thr Gln
            405                 410                 415

Tyr His His His His His His
            420

<210> SEQ ID NO 16
<211> LENGTH: 1282
<212> TYPE: DNA
<213> ORGANISM: Sus sp.

<400> SEQUENCE: 16
atggcctggt tgccctcta cctcctgagc cttctctggg ctgtggccgg aaccagcacc      60
cagacccgaa gctcatgctc tgttccctct gcagagcagc ccttggttaa tggcatccag     120
gtgctcatgg agcagtccgt gaccagctcg gccttcccaa accccagcat cctgattgcc     180
atgaacctgg ccggagccta caacacagag gcccaggagc tcctgactta caagctcatg     240
gctaccaaca cctccgacct gaccacaggt cagctcgccc tcaccatcat ggcactcacc     300
tcctcctgcc gagaccctgg gaacagaata gccattctac aggggcaaat ggagaactgg     360
gcacctccaa gccttgatac ccatgcttca accttctacg agccaagtct ggggatcctg     420

-continued

| | | |
|---|---|---|
| acgctgtgcc agaataaccc ggagaagacc ttaccgctag cagcccgttt tgccaagacc | 480 |
| ctgctggcca attcctctcc cttcaacatg gacacaggag caatggcaac cttggccctg | 540 |
| acctgtatgt acaacaagat ccccgtaggc tcagaggaag ggtacagagc cctgttcagt | 600 |
| caggtactga ggaatactgt ggagaatatc agcatgagga tccaagacaa cggaatcatt | 660 |
| ggaaacatct atagcactgg cctcgccatg caggctctct ctgtgacacc tgagcaacct | 720 |
| aacaaggagt gggactgcca gaagaccatg gatactgtac ttactgagat taaggagggg | 780 |
| aaattccaca ccccatggc cattgcccaa atcctccctt ccctgaaagg caagacctat | 840 |
| ctagatgtgc cccatgtgtc ttgcagccct ggtcatgagg tgccaccaac tctacccaac | 900 |
| caccccagcc ctgttcccac cccagcaccc aacatcaccg tcatatacac cataaataac | 960 |
| cagctgaggg gcgtggagct gctcttcaat gaaaccatca gtgttagtgt gaaaagagga | 1020 |
| tccgtgctac ttattgtcct ggaggaggca cagcgcaaaa accccaagtt caaatttgaa | 1080 |
| acgacaatga cgtcctgggg accggtggtc tcttctatta caatatcgc tgaaaatgtc | 1140 |
| aaccacagga cgtactggca gtttctgagt ggccaaacgc ccttaaacga aggagttgcg | 1200 |
| gactatatac ccttcaacca cgagcacatc acagccaatt tcacacagta ccatcatcac | 1260 |
| catcaccatt aactcgagga tt | 1282 |

<210> SEQ ID NO 17
<211> LENGTH: 1269
<212> TYPE: DNA
<213> ORGANISM: Sus sp.

<400> SEQUENCE: 17

| | | |
|---|---|---|
| atggtgatgg tgatgatggt actgtgtgaa attggctgtg atgtgctcgt ggttgaaggg | 60 |
| tatatagtcc gcaactcctt cgtttaaggg cgtttggcca ctcagaaact gccagtacgt | 120 |
| cctgtggttg acattttcag cgatattgtt aatagaagag accaccggtc cccaggacgt | 180 |
| cattgtcgtt tcaaatttga acttggggtt tttgcgctgt gcctcctcca ggacaataag | 240 |
| tagcacggat cctcttttca cactaacact gatggtttca ttgaagagca gctccacgcc | 300 |
| cctcagctgg ttatttatgg tgtatatgac ggtgatgttg ggtgctgggg tgggaacagg | 360 |
| gctggggtgg ttgggtagag ttggtggcac ctcatgacca gggctgcaag acacatgggg | 420 |
| cacatctaga taggtcttgc cttttcaggga agggaggatt tgggcaatgg ccatggggtt | 480 |
| gtggaatttc ccctccttaa tctcagtaag tacagtatcc atggtcttct ggcagtccca | 540 |
| ctccttgtta ggttgctcag gtgtcacaga gagagcctgc atggcgaggc cagtgctata | 600 |
| gatgttttcca atgattccgt tgtcttggat cctcatgctg atattctcca cagtattcct | 660 |
| cagtacctga ctgaacaggg ctctgtaccc ttcctctgag cctacgggga tcttgttgta | 720 |
| catacaggtc agggccaagg ttgccattgc tcctgtgtcc atgttgaagg gagaggaatt | 780 |
| ggccagcagg gtcttggcaa aacgggctgc tagcggtaag gtcttctccg ggttattctg | 840 |
| gcacagcgtc aggatcccca gacttggctc gtagaaggtt gaagcatggg tatcaaggct | 900 |
| tggaggtgcc cagttctcca tttgcccctg tagaatggct attctgttcc cagggtctcg | 960 |
| gcaggaggag gtgagtgcca tgatggtgag ggcgagctga cctgtggtca ggtcggaggt | 1020 |
| gttggtagcc atgagcttgt aagtcaggag ctcctgggcc tctgtgttgt aggctccggc | 1080 |
| caggttcatg gcaatcagga tgctgggggtt tgggaaggcc gagctggtca cggactgctc | 1140 |
| catgagcacc tggatgccat taaccaaggg ctgctctgca gagggaacag agcatgagct | 1200 |
| tcgggtctgg gtgctggttc cggccacagc ccagagaagg ctcaggaggt agagggcaaa | 1260 | ccaggccat                                                           1269

<210> SEQ ID NO 18
<211> LENGTH: 423
<212> TYPE: PRT
<213> ORGANISM: Sus sp.

<400> SEQUENCE: 18

Met Ala Trp Phe Ala Leu Tyr Leu Leu Ser Leu Leu Trp Ala Val Ala
1               5                   10                  15

Gly Thr Ser Thr Gln Thr Arg Ser Ser Cys Ser Val Pro Ser Ala Glu
            20                  25                  30

Gln Pro Leu Val Asn Gly Ile Gln Val Leu Met Glu Gln Ser Val Thr
        35                  40                  45

Ser Ser Ala Phe Pro Asn Pro Ser Ile Leu Ile Ala Met Asn Leu Ala
    50                  55                  60

Gly Ala Tyr Asn Thr Glu Ala Gln Glu Leu Leu Thr Tyr Lys Leu Met
65                  70                  75                  80

Ala Thr Asn Thr Ser Asp Leu Thr Thr Gly Gln Leu Ala Leu Thr Ile
                85                  90                  95

Met Ala Leu Thr Ser Ser Cys Arg Asp Pro Gly Asn Arg Ile Ala Ile
            100                 105                 110

Leu Gln Gly Gln Met Glu Asn Trp Ala Pro Ser Leu Asp Thr His
        115                 120                 125

Ala Ser Thr Phe Tyr Glu Pro Ser Leu Gly Ile Leu Thr Leu Cys Gln
    130                 135                 140

Asn Asn Pro Glu Lys Thr Leu Pro Leu Ala Ala Arg Phe Ala Lys Thr
145                 150                 155                 160

Leu Leu Ala Asn Ser Ser Pro Phe Asn Met Asp Thr Gly Ala Met Ala
                165                 170                 175

Thr Leu Ala Leu Thr Cys Met Tyr Asn Lys Ile Pro Val Gly Ser Glu
            180                 185                 190

Glu Gly Tyr Arg Ala Leu Phe Ser Gln Val Leu Arg Asn Thr Val Glu
        195                 200                 205

Asn Ile Ser Met Arg Ile Gln Asp Asn Gly Ile Ile Gly Asn Ile Tyr
    210                 215                 220

Ser Thr Gly Leu Ala Met Gln Ala Leu Ser Val Thr Pro Glu Gln Pro
225                 230                 235                 240

Asn Lys Glu Trp Asp Cys Gln Lys Thr Met Asp Thr Val Leu Thr Glu
                245                 250                 255

Ile Lys Glu Gly Lys Phe His Asn Pro Met Ala Ile Ala Gln Ile Leu
            260                 265                 270

Pro Ser Leu Lys Gly Lys Thr Tyr Leu Asp Val Pro His Val Ser Cys
        275                 280                 285

Ser Pro Gly His Glu Val Pro Pro Thr Leu Pro Asn His Pro Ser Pro
    290                 295                 300

Val Pro Thr Pro Ala Pro Asn Ile Thr Val Ile Tyr Thr Ile Asn Asn
305                 310                 315                 320

Gln Leu Arg Gly Val Glu Leu Leu Phe Asn Glu Thr Ile Ser Val Ser
                325                 330                 335

Val Lys Arg Gly Ser Val Leu Leu Ile Val Leu Glu Glu Ala Gln Arg
            340                 345                 350

Lys Asn Pro Lys Phe Lys Phe Glu Thr Thr Met Thr Ser Trp Gly Pro
        355                 360                 365

Val Val Ser Ser Ile Asn Asn Ile Ala Glu Asn Val Asn His Arg Thr

```
                370             375             380
Tyr Trp Gln Phe Leu Ser Gly Gln Thr Pro Leu Asn Glu Gly Val Ala
385             390             395             400

Asp Tyr Ile Pro Phe Asn His Glu His Ile Thr Ala Asn Phe Thr Gln
            405             410             415

Tyr His His His His His
            420

<210> SEQ ID NO 19
<211> LENGTH: 18
<212> TYPE: PRT
<213> ORGANISM: Sus sp.

<400> SEQUENCE: 19

Met Ala Trp Phe Ala Leu Tyr Leu Leu Ser Leu Leu Trp Ala Val Ala
1               5                   10                  15

Gly Thr

<210> SEQ ID NO 20
<211> LENGTH: 1200
<212> TYPE: DNA
<213> ORGANISM: Sus sp.

<400> SEQUENCE: 20
agcacccaga cccgaagctc atgctctgtt ccctctgcag agcagccctt ggttaatggc      60
atccaggtgc tcatggagca gtccgtgacc agctcggcct ccccaaaccc cagcatcctg     120
attgccatga acctggccgg agcctacaac acagaggccc aggagctcct gacttacaag     180
ctcatggcta ccaacacctc cgacctgacc acaggtcagc tcgccctcac catcatggca     240
ctcacctcct cctgccgaga ccctgggaac agaatagcca ttctacaggg gcaaatggag     300
aactgggcac ctccaagcct tgatacccat gcttcaacct tctacagagcc aagtctgggg    360
atcctgacgc tgtgccagaa taacccggag aagaccttac cgctagcagc ccgttttgcc     420
aagaccctgc tggccaattc ctctccctc aacatggaca caggagcaat ggcaaccttg      480
gccctgacct gtatgtacaa caagatcccc gtaggctcag aggaagggta cagagccctg     540
ttcagtcagg tactgaggaa tactgtggag aatatcagca tgaggatcca agacaacgga     600
atcattggaa acatctatag cactggcctc gccatgcagg ctctctctgt gacacctgag     660
caacctaaca aggagtggga ctgccagaag accatggata ctgtacttac tgagattaag     720
gaggggaaat ccacaacccc catggccatt gcccaaatcc tcccttccct gaaaggcaag     780
acctatctag atgtgcccca tgtgtcttgc agccctggtc atgaggtgcc accaactcta     840
cccaaccacc ccagccctgt tcccaccca gcacccaaca tcaccgtcat atacaccata     900
aataaccagc tgaggggcgt ggagctgctc ttcaatgaaa ccatcagtgt tagtgtgaaa     960
agaggatccg tgctacttat tgtcctggag gaggcacagc gcaaaaaccc caagttcaaa    1020
tttgaaacga caatgacgtc ctggggaccg gtggtctctt ctattaacaa tatcgctgaa    1080
aatgtcaacc acaggacgta ctggcagttt ctgagtggcc aaacgccctt aaacgaagga    1140
gttgcggact atatacctct caaccacgag acatcacag ccaatttcac acagtactaa     1200

<210> SEQ ID NO 21
<211> LENGTH: 1200
<212> TYPE: DNA
<213> ORGANISM: Sus sp.

<400> SEQUENCE: 21
```

-continued

```
ttagtactgt gtgaaattgg ctgtgatgtg ctcgtggttg aagggtatat agtccgcaac     60
tccttcgttt aagggcgttt ggccactcag aaactgccag tacgtcctgt ggttgacatt    120
ttcagcgata ttgttaatag aagagaccac cggtccccag gacgtcattg tcgtttcaaa    180
tttgaacttg gggttttttgc gctgtgcctc ctccaggaca ataagtagca cggatcctct    240
tttcacacta acactgatgg tttcattgaa gagcagctcc acgcccctca gctggttatt    300
tatggtgtat atgacggtga tgttgggtgc tggggtggga acagggctgg ggtgttgggg    360
tagagttggt ggcacctcat gaccagggct gcaagacaca tggggcacat ctagataggt    420
cttgcctttc agggaaggga ggatttgggc aatggccatg gggttgtgga atttcccctc    480
cttaatctca gtaagtacag tatccatggt cttctggcag tcccactcct tgttaggttg    540
ctcaggtgtc acagagagag cctgcatggc gaggccagtg ctatagatgt tccaatgat    600
tccgttgtct tggatcctca tgctgatatt ctccacagta ttcctcagta cctgactgaa    660
cagggctctg tacccttcct ctgagcctac ggggatcttg ttgtacatac aggtcagggc    720
caaggttgcc attgctcctg tgtccatgtt gaagggagag gaattggcca gcagggtctt    780
ggcaaaacgg gctgctagcg gtaaggtctt ctccggggtta ttctggcaca gcgtcaggat    840
ccccagactt ggctcgtaga aggttgaagc atgggtatca aggcttggag gtgcccagtt    900
ctccatttgc ccctgtagaa tggctattct gttcccaggg tctcggcagg aggaggtgag    960
tgccatgatg gtgagggcga gctgacctgt ggtcaggtcg gaggtgttgg tagccatgag   1020
cttgtaagtc aggagctcct gggcctctgt gttgtaggct ccggccaggt tcatggcaat   1080
caggatgctg gggtttggga aggccagct ggtcacggac tgctccatga gcacctggat   1140
gccattaacc aagggctgct ctgcagaggg aacagagcat gagcttcggg tctgggtgct   1200
```

<210> SEQ ID NO 22
<211> LENGTH: 399
<212> TYPE: PRT
<213> ORGANISM: Sus sp.

<400> SEQUENCE: 22

Ser Thr Gln Thr Arg Ser Ser Cys Ser Val Pro Ser Ala Glu Gln Pro
1               5                   10                  15

Leu Val Asn Gly Ile Gln Val Leu Met Glu Gln Ser Val Thr Ser Ser
            20                  25                  30

Ala Phe Pro Asn Pro Ser Ile Leu Ile Ala Met Asn Leu Ala Gly Ala
        35                  40                  45

Tyr Asn Thr Glu Ala Gln Glu Leu Leu Thr Tyr Lys Leu Met Ala Thr
    50                  55                  60

Asn Thr Ser Asp Leu Thr Thr Gly Gln Leu Ala Leu Thr Ile Met Ala
65                  70                  75                  80

Leu Thr Ser Ser Cys Arg Asp Pro Gly Asn Arg Ile Ala Ile Leu Gln
                85                  90                  95

Gly Gln Met Glu Asn Trp Ala Pro Pro Ser Leu Asp Thr His Ala Ser
            100                 105                 110

Thr Phe Tyr Glu Pro Ser Leu Gly Ile Leu Thr Leu Cys Gln Asn Asn
        115                 120                 125

Pro Glu Lys Thr Leu Pro Leu Ala Ala Arg Phe Ala Lys Thr Leu Leu
    130                 135                 140

Ala Asn Ser Ser Pro Phe Asn Met Asp Thr Gly Ala Met Ala Thr Leu
145                 150                 155                 160

Ala Leu Thr Cys Met Tyr Asn Lys Ile Pro Val Gly Ser Glu Glu Gly
                165                 170                 175

```
Tyr Arg Ala Leu Phe Ser Gln Val Leu Arg Asn Thr Val Glu Asn Ile
            180                 185                 190

Ser Met Arg Ile Gln Asp Asn Gly Ile Ile Gly Asn Ile Tyr Ser Thr
        195                 200                 205

Gly Leu Ala Met Gln Ala Leu Ser Val Thr Pro Glu Gln Pro Asn Lys
    210                 215                 220

Glu Trp Asp Cys Gln Lys Thr Met Asp Thr Val Leu Thr Glu Ile Lys
225                 230                 235                 240

Glu Gly Lys Phe His Asn Pro Met Ala Ile Ala Gln Ile Leu Pro Ser
            245                 250                 255

Leu Lys Gly Lys Thr Tyr Leu Asp Val Pro His Val Ser Cys Ser Pro
                260                 265                 270

Gly His Glu Val Pro Pro Thr Leu Pro Asn His Pro Ser Pro Val Pro
            275                 280                 285

Thr Pro Ala Pro Asn Ile Thr Val Ile Tyr Thr Ile Asn Asn Gln Leu
    290                 295                 300

Arg Gly Val Glu Leu Leu Phe Asn Glu Thr Ile Ser Val Ser Val Lys
305                 310                 315                 320

Arg Gly Ser Val Leu Leu Ile Val Leu Glu Glu Ala Gln Arg Lys Asn
                325                 330                 335

Pro Lys Phe Lys Phe Glu Thr Thr Met Thr Ser Trp Gly Pro Val Val
            340                 345                 350

Ser Ser Ile Asn Asn Ile Ala Glu Asn Val Asn His Arg Thr Tyr Trp
            355                 360                 365

Gln Phe Leu Ser Gly Gln Thr Pro Leu Asn Glu Gly Val Ala Asp Tyr
    370                 375                 380

Ile Pro Phe Asn His Glu His Ile Thr Ala Asn Phe Thr Gln Tyr
385                 390                 395

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 23

His His His His His His
1               5
```

CLONING, EXPRESSION AND PURIFICATION OF RECOMBINANT PORCINE INTRINSIC FACTOR FOR USE IN DIAGNOSTIC ASSAY

CROSS-REFERENCE TO RELATED APPLICATION

The subject application is related to pending U.S. patent application Ser. No. 11/052,128 filed on Feb. 7, 2005.

BACKGROUND OF THE INVENTION

1. Field of the Invention

The present invention relates to a new method of producing porcine Intrinsic Factor as well as to the protein produced using this method. In particular, the vector comprising the DNA sequence encoding the protein is introduced into a mammalian host cell, for example, a Chinese Hamster Ovary (CHO) cell, for a time and under conditions sufficient for optimal expression of the protein.

2. Background Information

Anemia is the major disorder related to low serum vitamin B12 levels. Megaloblastic anemia (MA), characterized by elevated mean corpuscular volume (MCV), has been found to be due to vitamin B12 deficiency. The relationship between vitamin B12 levels and MA is not always clear in that some patients with MA will have normal vitamin B12 levels; conversely, many individuals with vitamin B12 deficiency are not afflicted with MA. Despite these complications, however, in the presence of MA (e.g., elevated MCV) there is usually serum vitamin B12 deficiency. A major cause of vitamin B12 deficiency is pernicious anemia. This disease is characterized by poor vitamin B12 uptake, resulting in below normal serum vitamin B12.

There a number of conditions that manifest themselves as low serum vitamin B12 levels, including iron deficiency, normal near-term pregnancy, vegetarianism, partial gastrectomy/ileal damage, oral contraception, parasitic competition, pancreatic deficiency, treated epilepsy, and advancing age. Disorders associated with elevated serum vitamin B12 levels include renal failure, liver disease, and myeloproliferative diseases.

Intrinsic Factor binds vitamin B12. This characteristic enables the detection of and measurement of the quantity of vitamin B12 in biological samples. In conventional preparation of Intrinsic Factor, the Intrinsic Factor protein is isolated from porcine tissue by means of an expensive, tedious, and time-consuming process.

cDNA cloning using reverse transcriptase-polymerase chain reaction technique (RT-PCR) is well-known in the art. The designing of primers based on homology known for this particular protein in other species (such as human, mouse and rat) and selecting the appropriate PCR conditions to obtain cDNA require a significant amount of planning and expertise in the PCR-based cloning technique.

U.S. Pat. No. 3,591,678 discloses a process for purifying Intrinsic Factor by a batch chromatography process that utilizes an ion exchange resin. Impure Intrinsic Factor is dissolved in a buffer solution having relatively low pH and ionic strength, and the resultant solution is contacted with a cellulosic exchange resin. The resin is separated from the solution and the purified Intrinsic Factor is eluted therefrom with a buffer solution having a higher pH and ionic strength than the buffer solution in which the impure Intrinsic Factor was dissolved.

U.S. Pat. No. 4,447,528 discloses a radioassay procedure and reagent kit therefore for detecting auto-blocking antibody, such as auto blocking antibody which interferes with the complexation of Intrinsic Factor with vitamin B12. A receptor, i.e., Intrinsic Factor, is immobilized on a support and the amount of ligand, i.e., vitamin B12, capable of binding therewith in the presence of a biological fluid sample is determined.

U.S. Pat. Nos. 5,227,311 and 5,459,242 disclose a method for purifying an aqueous Intrinsic Factor solution which contains R-protein. The method involves adding to the Intrinsic Factor solution an amount of colloidal silica to disperse lipid emulsion, an amount of cobinamide sufficient to bind substantially all of the R-protein in the solution and an amount of an Intrinsic Factor affinity resin sufficient to bind the Intrinsic Factor in the solution, washing the bound cobinamide and the R-protein from the resin, eluting the Intrinsic Factor from the resin, and dialyzing the eluted Intrinsic Factor. Also disclosed is a kit for conducting an assay for cobalamins which includes a conjugate of microparticles and purified Intrinsic Factor.

U.S. Pat. No. 5,350,674 discloses a non-isotopic competitive assay for vitamin B12, utilizing Intrinsic Factor labeled with horseradish peroxidase, by coupling via heterobifunctional cross-linking agents. In addition, a method for stabilizing the resultant conjugates by pretreatment with N-ethylmaleimide is disclosed.

Prior investigators have disclosed the cDNA sequences encoding human Intrinsic Factor (Genbank Accession No. M63154), mouse Intrinsic Factor (Genbank Accession No. L24191) and rat Intrinsic Factor (Genbank Accession No. J03577). The cDNA sequence of the porcine Intrinsic Factor is disclosed in U.S. Published Patent Application No. 2006/0177872 of Abbott Laboratories. This application also discloses a method of producing porcine Intrinsic Factor by the use of E. coli cells.

Porcine Intrinsic Factor is typically isolated from the tissue of the duodenum of a hog (e.g., Sus scrofa). This isolation is a tedious, expensive, and time-consuming procedure, and the yields are low. The native Intrinsic Factor isolated by currently used procedures lacks consistency in its purity and in its resulting performance in an immunoassay. Therefore, it would be desirable to produce porcine Intrinsic Factor in large quantities and to isolate porcine Intrinsic Factor in a single-step affinity isolation process. Recombinant protein produced in this manner would have consistent performance in a diagnostic immunoassay.

All patents and publications referred to herein are hereby incorporated in their entirety by reference.

SUMMARY OF THE INVENTION

The present invention encompasses a method of producing porcine Intrinsic Factor comprising the steps of: isolating a nucleic acid sequence comprising or complementary to a nucleotide sequence either encoding porcine Intrinsic Factor comprising an amino acid sequence having at least 85% identity to an amino acid sequence selected from the group consisting of SEQ ID NO: 5, SEQ ID NO: 18, and SEQ ID NO: 22 or having at least 85% identity to a nucleotide sequence selected from the group consisting of SEQ ID NO: 3, SEQ ID NO: 16, and SEQ ID NO: 20; constructing a vector comprising: i) the isolated nucleotide sequence operably linked to ii) a regulatory sequence; and introducing the vector into a host cell for a time and under conditions sufficient for expression of the porcine Intrinsic Factor, wherein the host cell is a mammalian cell. The mammalian cell may be, for example, a Chinease Hamster Ovary (CHO) cell. Further, the regulatory sequence may be, for example, a promoter. The amino acid sequence may have at least 90% identity to an amino acid sequence selected from the group consisting of SEQ ID NO: 5, SEQ ID NO: 18 and SEQ ID NO: 22. In this method, the nucleic acid sequence may have at least 90% identity to a nucleotide sequence selected from the group consisting of SEQ ID NO: 3, SEQ ID NO:16 and SEQ ID NO:20.

The present invention further includes a protein produced by one of the methods described above.

Additionally, the present invention includes a method of producing recombinant porcine Intrinsic Factor having at least 97% purity comprising the steps of: isolating a nucleic acid sequence comprising or complementary to a nucleotide sequence either encoding porcine Intrinsic Factor comprising an amino acid sequence having at least 85% identity to an amino acid sequence selected from the group consisting of SEQ ID NO: 5, SEQ ID NO: 18, and SEQ ID NO: 22 or having at least 85% identity to a nucleotide sequence selected from the group consisting of SEQ ID NO: 3, SEQ ID NO: 16, and SEQ ID NO: 20; constructing a vector comprising: i) the isolated nucleic acid sequence operably linked to ii) a regulatory sequence; introducing the vector into a host cell for a time and under conditions sufficient for expression of the porcine Intrinsic Factor, wherein the host cell is a mammalian cell, for example, a CHO cell; subjecting the expressed porcine Intrinsic Factor to a first affinity chromatography procedure; subjecting resulting porcine Intrinsic Factor to a second affinity chromatography procedure; and subjecting the resulting porcine Intrinsic Factor to a size exclusion chromatography procedure wherein resulting porcine Intrinsic Factor has a purity of at least 97%. The first affinity chromatography procedure may comprise use of a nickel column. The second affinity chromatography procedure may comprises use of a Vitamin B12 column. Further, the purity of the final product (i.e., the protein) may be 99%. The present invention also includes the protein produced by this method.

Also, the present invention encompasses a method of detecting Vitamin B12 in a test sample from a patient. This method comprises the steps of coating porcine Intrinsic Factor produced in accordance with the methods described above onto a solid phase; adding the test sample to the resulting coated solid phase for a time and under conditions sufficient to allow Vitamin B12 present in the test sample to bind to the porcine Intrinsic Factor coated on the solid phase; adding a conjugate to the bound intrinsic porcine factor, wherein the conjugate comprises an antibody attached to a signal-generating compound capable of generating a detectable signal; and detecting presence of the signal generated, such presence indicating presence of Vitamin B12 in the test sample, wherein the amount of Vitamin B12 in the sample is indirectly proportional to the signal generated by the signal-generating compound. The signal-generating compound may be, for example, a label such as acridinium. The solid phase may be, for example, a paramagnetic microparticle. Further, the mammalian cell used to produce the porcine Intrinsic Factor used in the method may be, for example, a CHO cell.

Intrinsic Factor isolated by methods currently used in the art provides an inconsistent result with respect to purity, and, consequently, performance in an assay. By employing the method and protein of this invention, recombinant Intrinsic Factor having consistent properties can be produced. Also, the method of this invention reduces cost and simplifies isolation. Furthermore, the results of the assays using porcine Intrinsic Factor show improved consistency.

BRIEF DESCRIPTION OF THE DRAWINGS

FIG. 3 illustrates binding data derived from the ARCHITECT® assay that measures the binding capacity of the recombinant porcine Intrinsic Factor (produced in CHO Cells), in terms of light units. In particular, the results establish that porcine Intrinsic Factor produced in CHO cells will bind Vitamin B12 in an immunoassay format on ARCHITECT®.

DETAILED DESCRIPTION OF THE INVENTION

Figure 1:
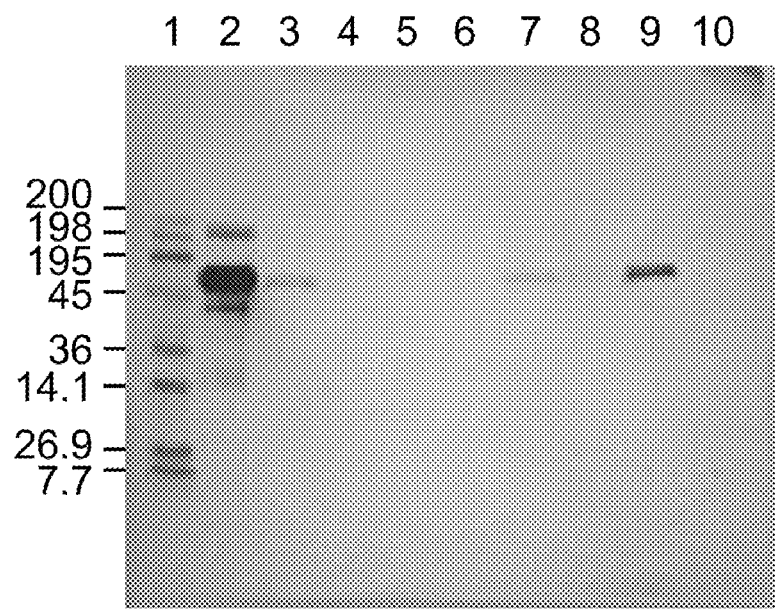
FIG. 1 illustrates Western-blot data that demonstrate binding of recombinant porcine Intrinsic Factor (produced in CHO cells) to Vitamin B12. In particular, this figure illustrates six CHO cell clones that produced functional porcine Intrinsic Factor.

For purposes of the present invention, the term "fragment", with respect to a nucleotide sequence, is defined as a contiguous sequence of approximately at least 6, preferably at least about 8, more preferably at least about 10 nucleotides, and even more preferably at least about 15 nucleotides corresponding to a region of the specified nucleotide sequence.

The invention also includes a purified polypeptide, produced according to the method described herein, which binds vitamin B12 and has at least about 70% amino acid similarity or identity, preferably at least about 80% amino acid similarity or identity and more preferably at least about 85% amino acid similarity or identity, even more preferably at least 90% identity and most preferably 95% identity to the amino acid sequences of SEQ ID NO: 5, SEQ ID NO: 18, or SEQ ID NO: 22 which are, in turn, encoded by nucleotide sequences described herein. (It should be noted that percentages failing within the above range are also considered to be within the scope of the present invention (e.g., 71%, 72%, 73%, 74%, 75%, 76%, 77%, 78%, 79%, 81%, 82%, 83% and 84% 86%, 87%, 88%, 89%, 91%, 92%, 93% and 94%).)

The term "identity" refers to the relatedness of two sequences on a nucleotide-by-nucleotide basis over a particular comparison window or segment. Thus, identity is defined as the degree of sameness, correspondence or equivalence between the same strands (either sense or antisense) of two DNA segments (or two amino acid sequences). "Percentage of sequence identity" is calculated by comparing two optimally aligned sequences over a particular region, determining the number of positions at which the identical base or amino acid occurs in both sequences in order to yield the number of matched positions, dividing the number of such positions by the total number of positions in the segment being compared and multiplying the result by 100. Optimal alignment of sequences may be conducted by the algorithm of Smith & Waterman, Appl. Math. 2:482 (1981), by the algorithm of Needleman & Wunsch, J. Mol. Biol. 48:443 (1970), by the method of Pearson & Lipman, Proc. Natl. Acad. Sci. (USA) 85:2444 (1988) and by computer programs which implement the relevant algorithms (e.g., Clustal Macaw Pileup (http://cmgm.stanford.edu./biochem218/11 Multiple.pdf; Higgins et al., CABIOS. 5L151-153 (1989)), FASTDB (Intelligenetics), BLAST (National Center for Biomedical Information; Altschul et al., Nucleic Acids Research 25:3389-3402 (1997)), PILEUP (Genetics Computer Group, Madison, Wis.) or GAP, BESTFIT, FASTA and TFASTA (Wisconsin Genetics Software Package Release 7.0, Genetics Computer Group, Madison, Wis.). (See U.S. Pat. No. 5,912,120.)

For purposes of the present invention, the term "complementarity" is defined as the degree of relatedness between two DNA segments. It is determined by measuring the ability of the sense strand of one DNA segment to hybridize with the anti-sense strand of the other DNA segment, under appropriate conditions, to form a double helix. The term "complement" is defined as a sequence which pairs to a given sequence based upon the canonic base-pairing rules. For example, a sequence A-G-T in one nucleotide strand is "complementary" to T-C-A in the other strand.

In the double helix, adenine appears in one strand, thymine appears in the other strand. Similarly, wherever guanine is found in one strand, cytosine is found in the other. The greater the relatedness between the nucleotide sequences of two DNA segments, the greater the ability to form hybrid duplexes between the strands of the two DNA segments.

The term "similarity", with respect to two amino acid sequences, is defined as the presence of a series of identical as well as conserved amino acid residues in both sequences. The higher the degree of similarity between two amino acid sequences, the higher the correspondence, sameness or equivalence of the two sequences. (The term "identity", with respect to two amino acid sequences, is defined as the presence of a series of exactly alike or invariant amino acid residues in both sequences.) The definitions of "complementarity", "identity" and "similarity" are well known to those of ordinary skill in the art.

The phrase "encoded by" refers to a nucleic acid sequence which codes for a polypeptide sequence, wherein the polypeptide sequence or a portion thereof contains an amino acid sequence of at least 3 amino acids, more preferably at least 8 amino acids, and even more preferably at least 15 amino acids from a polypeptide encoded by the nucleic acid sequence.

The present invention also encompasses an isolated nucleotide sequence which encodes porcine Intrinsic Factor and that is hybridizable, under moderately stringent conditions, to a nucleic acid having a nucleotide sequence comprising or complementary to the nucleotide sequences described herein (see SEQ ID NO: 3, SEQ ID NO: 16, and SEQ ID NO: 20). Further, the present invention also includes those nucleotide sequences or fragments thereof having at least 70%, preferably at least 80%, more preferably at least 85%, even more preferably at least 90% and most preferably at least 95% sequence identity to the nucleotide sequences of SEQ ID NO:3, SEQ ID NO:16 or SEQ ID NO:20. (It should again be noted that percentages failing within the above range are also considered to be within the scope of the present invention (e.g., 71%, 72%, 73%, 74%, 75%, 76%, 77%, 78%, 79%, 81%, 82%, 83% and 84%, 86%, 87%, 88%, 89%, 91%, 92%, 93% and 94%).)

A nucleic acid molecule is "hybridizable" to another nucleic acid molecule when a single-stranded form of the nucleic acid molecule can anneal to the other nucleic acid molecule under the appropriate conditions of temperature and ionic strength (see Sambrook et al., "Molecular Cloning: A Laboratory Manual, Second Edition (1989), Cold Spring Harbor Laboratory Press, Cold Spring Harbor, N.Y.)). The conditions of temperature and ionic strength determine the "stringency" of the hybridization.

The term "hybridization" as used herein is generally used to mean hybridization of nucleic acids at appropriate conditions of stringency as would be readily evident to those skilled in the art depending upon the nature of the probe sequence and target sequences. Conditions of hybridization and washing are well known in the art, and the adjustment of conditions depending upon the desired stringency by varying incubation time, temperature, and/or ionic strength of the solution are readily accomplished. See, for example, Sambrook, J. et al., Molecular Cloning: A Laboratory Manual, 2nd edition, Cold Spring Harbor Press, Cold Spring Harbor, N.Y., 1989, as noted above and incorporated herein by reference. (See also Short Protocols in Molecular Biology, ed. Ausubel et al. and Tijssen, Techniques in Biochemistry and Molecular Biology-Hybridization with Nucleic Acid Probes, "Overview of principles of hybridization and the strategy of nucleic acid assays" (1993), both incorporated herein by reference.) Specifically, the choice of conditions is dictated by the length of the sequences being hybridized, in particular, the length of the probe sequence, the relative G-C content of the nucleic acids and the amount of mismatches to be permitted. Low stringency conditions are preferred when partial hybridization between strands that have lesser degrees of complementarity is desired. When perfect or near perfect complementarity is desired, high stringency conditions are preferred. For typical high stringency conditions, the hybridization solution contains 6×S.S.C., 0.01 M EDTA, 1× Denhardt's solution and 0.5% SDS. Hybridization is carried out at about 68 degrees Celsius for about 3 to 4 hours for fragments of cloned DNA and for about 12 to about 16 hours for total eukaryotic DNA. For moderate stringencies, one may utilize filter pre-hybridizing and hybridizing with a solution of 3× sodium chloride, sodium citrate (SSC), 50% formamide (0.1 M of this buffer at pH 7.5) and 5× Denhardt's solution. One may then pre-hybridize at 37 degrees Celsius for 4 hours, followed by hybridization at 37 degrees Celsius with an amount of labeled probe equal to 3,000,000 cpm total for 16 hours, followed by a wash in 2×SSC and 0.1% SDS solution, a wash of 4 times for 1 minute each at room temperature and 4 times at 60 degrees Celsius for 30 minutes each. Subsequent to drying, one exposes to film. For lower stringencies, the temperature of hybridization is reduced to about 12 degrees Celsius below the melting temperature ($T_m$) of the duplex. The $T_m$ is known to be a function of the G-C content and duplex length as well as the ionic strength of the solution.

"Hybridization" requires that two nucleic acids contain complementary sequences. However, depending on the stringency of the hybridization, mismatches between bases may occur. As noted above, the appropriate stringency for hybridizing nucleic acids depends on the length of the nucleic acids and the degree of complementation. Such variables are well known in the art. More specifically, the greater the degree of similarity or homology between two nucleotide sequences, the greater the value of Tm for hybrids of nucleic acids having those sequences. For hybrids of greater than 100 nucleotides in length, equations for calculating Tm have been derived (see Sambrook et al., supra). For hybridization with shorter nucleic acids, the position of mismatches becomes more important, and the length of the oligonucleotide determines its specificity (see Sambrook et al., supra).

As used herein, the phrase "isolated nucleic acid fragment or sequence" means a polymer of RNA or DNA that is single-stranded or double-stranded, optionally containing synthetic, non-natural or altered nucleotide bases. An isolated nucleic acid fragment in the form of a polymer of DNA may be comprised of one or more segments of cDNA, genomic DNA or synthetic DNA. (The term "fragment", with respect to a specified polynucleotide, refers to a polynucleotide sequence which comprises a contiguous sequence of approximately at least about 6 nucleotides, preferably at least about 8 nucleotides, more preferably at least about 10 nucleotides, and even more preferably at least about 15 nucleotides, and most preferable at least about 25 nucleotides identical or complementary to a region of the specified nucleotide sequence.) Nucleotides (usually found in their 5'-monophosphate form) are referred to by their single letter designation as follows:

"A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The phrases "fragment or subfragment that is functionally equivalent" and "functionally equivalent fragment or subfragment" are used interchangeably herein. These phrases refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric constructs to produce the desired phenotype in a transformed plant. Chimeric constructs can be designed for use in co-suppression or antisense by linking a nucleic acid fragment or subfragment thereof, whether or not it encodes an active enzyme, in the appropriate orientation relative to a plant promoter sequence.

The terms/phrases "homology", "homologous", "substantially similar" and "corresponding substantially" are used interchangeably herein. They refer to nucleic acid fragments wherein changes in one or more nucleotide bases does not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

The term "gene" refers to a nucleic acid fragment that expresses a specific protein, including regulatory sequences preceding (5' non-coding sequences) and following (3' non-coding sequences) the coding sequence.

The phrase "native gene" refers to a gene as found in nature with its own regulatory sequences. In contrast, the phrase "chimeric construct" refers to a combination of nucleic acid fragments that are not normally found together in nature. Accordingly, a chimeric construct may comprise regulatory sequences and coding sequences that are derived from different sources, or regulatory sequences and coding sequences derived from the same source, but arranged in a manner different than that normally found in nature. (The term "isolated" means that the sequence is removed from its natural environment.)

The phrase "foreign gene" refers to a gene not normally found in the host organism, but that is introduced into the host organism by gene transfer. Foreign genes can comprise native genes inserted into a non-native organism, or chimeric constructs. The term "transgene" means a gene that has been introduced into the genome by a transformation procedure.

The phrase "coding sequence" refers to a DNA sequence that codes for a specific amino acid sequence. The term "regulatory sequences" refers to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

The term "regulatory sequence" (e.g., a promoter) refers to a DNA sequence capable of controlling the expression of a coding sequence or functional RNA. The sequence consists of proximal and more distal upstream elements, the latter elements often referred to as enhancers. The term "enhancer" means a DNA sequence that can stimulate promoter activity and may be an innate element of the promoter or a heterologous element inserted to enhance the level or tissue-specificity of a promoter. Promoters can be located within the transcribed portions of genes, and/or downstream of the transcribed sequences. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters that cause a gene to be expressed in most host cell types at most times are commonly referred to as "constitutive promoters". It is further recognized that since in most cases the exact boundaries of regulatory sequences have not been completely defined, DNA fragments of some variation may have identical promoter activity.

The term "intron" means an intervening sequence in a gene that does not encode a portion of the protein sequence. Thus, such sequences are transcribed into RNA but are then excised and are not translated. The term is also used for the excised RNA sequences. The term "exon" means a portion of the gene sequence that is transcribed and is found in the mature messenger RNA derived from the gene, but is not necessarily a part of the sequence that encodes the final gene product.

The phrase "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The phrase "3' non-coding sequences" refers to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., *Plant Cell* 1:671-680 (1989).

The phrase "RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. The phrase "messenger RNA (mRNA)" refers to the RNA that is without introns and that can be translated into protein by the cell. The term "cDNA" refers to a DNA that is complementary to and synthesized from a mRNA template using the enzyme reverse transcriptase. The cDNA can be single-stranded or converted into the double-stranded form using the Klenow fragment of DNA polymerase I. The phrase "sense RNA" refers to RNA transcript that includes the mRNA and can be translated into protein within a cell or in vitro.

The phrase "antisense RNA" refers to an RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. The phrase "functional RNA" refers to antisense RNA, ribozyme RNA, or other RNA that may not be translated but yet has an effect on cellular processes. The term "complement" and the phrase "reverse complement" are used interchangeably herein with respect to mRNA transcripts, and are meant to define the antisense RNA of the message.

The phrase "endogenous RNA" refers to any RNA which is encoded by any nucleic acid sequence present in the genome of the host prior to transformation with the recombinant construct of the present invention, whether naturally-occurring or non-naturally occurring, i.e., introduced by recombinant means, mutagenesis, etc.

The phrase "non-naturally occurring" means artificial, not consistent with what is normally found in nature.

The phrase "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA. "Operably linked" sequences include both expression control sequences that are contiguous with the gene of interest and expression control sequences that act in trans or at a distance to control the gene of interest. The phrase "expression control sequence" as used herein refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The phrase "control sequences" is intended to include components whose presence is essential for expression and processing, and can also include additional components whose presence is advantageous, for example, leader sequences and fusion partner sequences.

The term "expression", as used herein, refers to the production of a functional end-product. Expression of a gene involves transcription of the gene and translation of the mRNA into a precursor or mature protein. "Antisense inhibition" refers to the production of antisense RNA transcripts capable of suppressing the expression of the target protein. The term "co-suppression" refers to the production of sense RNA transcripts capable of suppressing the expression of identical or substantially similar foreign or endogenous genes (U.S. Pat. No. 5,231,020).

The phrase "mature protein" refers to a post-translationally processed polypeptide; i.e., one from which any pre- or propeptides present in the primary translation product have been removed. The term "precursor" protein refers to the primary product of translation of mRNA; i.e., with pre- and pro-peptides still present. Pre- and pro-peptides may be but are not limited to intracellular localization signals.

The term "transformation", as defined herein, refers to any process by which exogenous DNA enters a host cell. Transformation may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells that transiently express the inserted DNA or RNA for limited periods of time.

The phrase "stable transformation" refers to the transfer of a nucleic acid fragment into a genome of a host organism, resulting in genetically stable inheritance. In contrast, the phrase "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms. The term "transformation" as used herein refers to both stable transformation and transient transformation.

Standard recombinant DNA and molecular cloning techniques used herein are well known in the art and are described more fully in Sambrook, J., Fritsch, E. F. and Maniatis, T., *Molecular Cloning: A Laboratory Manual*; Cold Spring Harbor Laboratory Press: Cold Spring Harbor, 1989 (hereinafter "Sambrook").

The term "recombinant" refers to an artificial combination of two otherwise separated segments of sequence, e.g., by chemical synthesis or by the manipulation of isolated segments of nucleic acids by genetic engineering techniques.

The term "PCR" and the phrase "Polymerase Chain Reaction" refers to a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

Polymerase chain reaction ("PCR") is a powerful technique used to amplify DNA millions of fold, by repeated replication of a template, in a short period of time. (Mullis et al., *Cold Spring Harbor Symp. Quant. Biol.* 51:263-273 (1986); Erlich et al., European Patent Application No. 50,424; European Patent Application No. 84,796; European Patent Application No. 258,017; European Patent Application No. 237,362; Mullis, European Patent Application No. 201,184; Mullis et al., U.S. Pat. No. 4,683,202; Erlich, U.S. Pat. No. 4,582,788; and Saiki et al., U.S. Pat. No. 4,683,194). The process utilizes sets of specific in vitro synthesized oligonucleotides to prime DNA synthesis. The design of the primers is dependent upon the sequences of DNA that are desired to be analyzed. The technique is carried out through many cycles (usually 20-50) of melting the template at high temperature, allowing the primers to anneal to complementary sequences within the template and then replicating the template with DNA polymerase.

The products of PCR reactions are analyzed by separation in agarose gels followed by ethidium bromide staining and visualization with UV transillumination. Alternatively, radioactive dNTPs can be added to the PCR in order to incorporate label into the products. In this case the products of PCR are visualized by exposure of the gel to x-ray film. The added advantage of radiolabeling PCR products is that the levels of individual amplification products can be quantitated.

The term "RT-PCR" means a combination of Reverse Transcription and PCR. Reverse transcription is a process where RNA is used as a starting material to make DNA using an enzyme called Reverse Transcriptase. The first strand of DNA that is made during reverse transcription is used as the starting material for the PCR reactions that follow.

The phrases "recombinant construct", "expression construct" and "recombinant expression construct" are used interchangeably herein. These phrases refer to a functional unit of genetic material that can be inserted into the genome of a cell using standard methodology well known to one skilled in the art. Such construct may be itself or may be used in conjunction with a vector. If a vector is used then the choice of vector is dependent upon the method that will be used to transform the host cell as is well known to those skilled in the art. For example, a plasmid, cosmid or bacteriophage can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., (1985) *EMBO J.* 4:2411-2418; De Almeida et al., (1989) *Mol. Gen. Genetics* 218:78-86), and thus that multiple events must be screened in order to obtain proteins displaying the desired expression level and pattern. Such screening may be accomplished by Southern analysis of DNA, Northern analysis of mRNA expression, Western analysis of protein expression, or phenotypic analysis.

The term "polypeptide" as used herein, refers to any polymeric chain of amino acids. The terms "peptide" and "protein" are used interchangeably with the term polypeptide and also refer to a polymeric chain of amino acids. The term "polypeptide" encompasses native or artificial proteins, protein fragments and polypeptide analogs of a protein sequence. A polypeptide may be monomeric or polymeric.

The phrases "isolated protein" and "isolated polypeptide" refer to a protein or polypeptide that by virtue of its origin or source of derivation is not associated with naturally associated components that accompany it in its native state; is substantially free of other proteins from the same species; is expressed by a cell from a different species; or does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The phrases "specific binding" and "specifically binding", as used herein, in reference to the interaction of an antibody, a protein, or a peptide with a second chemical species, mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art, non-limiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The phrase "antigen-binding portion" of an antibody (or simply "antibody portion"), as used herein, refers to one or more fragments of an antibody that retain the ability to specifically bind to an antigen (e.g., hIL-18). It has been shown that the antigen-binding function of an antibody can be performed by fragments of a full-length antibody. Such antibody embodiments may also be bispecific, dual specific, or multispecific formats; specifically binding to two or more different antigens. Examples of binding fragments encompassed within the phrase "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the phrase "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poijak, R. J., et al. (1994) *Structure* 2:1121-1123). Such antibody binding portions are known in the art (Kontermann and Dubel eds., *Antibody Engineering* (2001) Springer-Verlag. New York. 790 pp. (ISBN 3-540-41354-5).

Still further, an antibody or antigen-binding portion thereof may be part of a larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv molecules (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

The phrase "isolated antibody", as used herein, is intended to refer to an antibody that is substantially free of other antibodies having different antigenic specificities (e.g., an isolated antibody that specifically binds hIL-18 is substantially free of antibodies that specifically bind antigens other than hIL-18). An isolated antibody that specifically binds hIL-18 may, however, have cross-reactivity to other antigens, such as IL-18 molecules from other species. Moreover, an isolated antibody may be substantially free of other cellular material and/or chemicals.

A "monoclonal antibody" as used herein is intended to refer to a preparation of antibody molecules which share a common heavy chain and common light chain amino acid sequence, in contrast with "polyclonal" antibody preparations which contain a mixture of different antibodies. Monoclonal antibodies can be generated by several novel technologies like phage, bacteria, yeast or ribosomal display, as well as classical methods exemplified by hybridoma-derived antibodies (e.g., an antibody secreted by a hybridoma prepared by hybridoma technology, such as the standard Kohler and Milstein hybridoma methodology ((1975) *Nature* 256:495-497). Thus, a non-hybridoma-derived antibody of the invention is still referred to as a monoclonal antibody although it may have been derived by non-classical methodologies.

The phrase "recombinant antibody" refers to antibodies that are prepared, expressed, created or isolated by recombinant means, such as antibodies expressed using a recombinant expression vector transfected into a host cell, antibodies isolated from a recombinant, combinatorial antibody library, antibodies isolated from an animal (e.g., a mouse) that is transgenic for human immunoglobulin genes (see, e.g., Taylor et al. (1992) *Nucleic Acids Research* 20:6287-6295) or antibodies prepared, expressed, created or isolated by any other means that involves splicing of particular immunoglobulin gene sequences (such as human immunoglobulin gene sequences) to other DNA sequences. Examples of recombinant antibodies include chimeric, CDR-grafted and humanized antibodies.

The phrase "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo, for example in the CDRs and in particular CDR3. However, the phrase "human antibody", as used herein, is not intended to include antibodies in which CDR sequences derived from the germline of another mammalian species, such as a mouse, have been grafted onto human framework sequences.

The phrase "recombinant human antibody", as used herein, is intended to include all human antibodies that are prepared, expressed, created or isolated by recombinant means, such as antibodies expressed using a recombinant expression vector transfected into a host cell, antibodies isolated from a recombinant, combinatorial human antibody library (Hoogenboom H. R., (1997) *TIB Tech.* 15:62-70; Azzazy H., and Highsmith W. E., (2002) *Clin. Biochem.* 35:425-445; Gavilondo J. V., and Larrick J. W. (2002) *BioTechniques* 29:128-145; Hoogenboom H., and Chames P. (2000) *Immunology Today* 21:371-378), antibodies isolated from an animal (e.g., a mouse) that is transgenic for human immunoglobulin genes (see e.g., Taylor, L. D., et al. (1992) Nucl. Acids Res. 20:6287-6295; Kellermann S-A., and Green L. L. (2002) *Current Opinion in Biotechnology* 13:593-597; Little M. et al (2000) *Immunology Today* 21:364-370) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The phrase "chimeric antibody" refers to antibodies which comprise heavy and light chain variable region sequences from one species and constant region sequences from another species, such as antibodies having murine heavy and light chain variable regions linked to human constant regions.

The phrase "CDR-grafted antibody" refers to antibodies which comprise heavy and light chain variable region sequences from one species but in which the sequences of one or more of the CDR regions of $V_H$ and/or VL are replaced with CDR sequences of another species, such as antibodies having murine heavy and light chain variable regions in which one or more of the murine CDRs (e.g., CDR3) has been replaced with human CDR sequences.

The phrase "humanized antibody" refers to antibodies which comprise heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences.

The term "epitope" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules.

The phrase "crystallized binding protein" as used herein, refers to a polypeptide that exists in the form of a crystal. Crystals are one form of the solid state of matter, which is distinct from other forms such as the amorphous solid state or the liquid crystalline state. Crystals are composed of regular, repeating, three-dimensional arrays of atoms, ions, molecules (e.g., proteins such as antibodies), or molecular assemblies (e.g., antigen/antibody complexes). These three-dimensional arrays are arranged according to specific mathematical relationships that are well-understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See Giege, R. and Ducruix, A. Barrett, Crystallization of Nucleic Acids and Proteins, a Practical Approach, 2nd ea., pp. 20 1-16, Oxford University Press, New York, N.Y., (1999)."

The term "polynucleotide" as referred to herein means a polymeric form of two or more nucleotides, either ribonucleotides or deoxynucleotides or a modified form of either type of nucleotide. The term includes single and double stranded forms of DNA but preferably is double-stranded DNA.

The phrase "isolated polynucleotide" as used herein means a polynucleotide (e.g., of genomic, cDNA, or synthetic origin, or some combination thereof) that, by virtue of its origin, the "isolated polynucleotide" is not associated with all or a portion of a polynucleotide with which the "isolated polynucleotide" is found in nature; is operably linked to a polynucleotide that it is not linked to in nature; or does not occur in nature as part of a larger sequence.

The term "vector", as used herein, is intended to refer to a nucleic acid molecule capable of transporting another nucleic acid to which it has been linked. One type of vector is a "plasmid", which term refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, the terms "plasmid" and "vector" may be used interchangeably, as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The phrase "recombinant host cell" (or simply "host cell"), as used herein, is intended to refer to a cell into which exogenous DNA has been introduced. It should be understood that such phrases are intended to refer not only to the particular subject cell, but, to the progeny of such a cell. Because certain modifications may occur in succeeding generations due to either mutation or environmental influences, such progeny may not, in fact, be identical to the parent cell, but are still included within the scope of the phrase "host cell" as used herein. Preferably host cells include prokaryotic and eukaryotic cells selected from any of the Kingdoms of life. Preferred eukaryotic cells include protist, fungal, plant and animal cells. Most preferably host cells include but are not limited to the prokaryotic cell line *E. coli*; mammalian cell lines CHO and COS; the insect cell line Sf9; and the fungal cell *Saccharomyces cerevisiae*.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference for any purpose.

The term "primer" means an oligonucleotide or a short single-stranded nucleic acid molecule that binds to the DNA sequence of interest and acts as a starting point for the synthesis of nucleic acids from the DNA sequence of interest.

The term "sample", as used herein, is used in its broadest sense. A "biological sample", as used herein, includes, but is not limited to, any quantity of a substance from a living thing or formerly living thing. Such living things include, but are not limited to, humans, mice, rats, monkeys, dogs, rabbits and other animals. Such substances include, but are not limited to, blood, serum, urine, synovial fluid, cells, organs, tissues, bone marrow, lymph nodes and spleen.

The method for producing the porcine Intrinsic Factor of this invention involves the following steps:
  (a) isolating total RNA from porcine stomach tissue;
  (b) cloning cDNA encoding porcine Intrinsic Factor by RT-PCR;
  (c) inserting porcine Intrinsic Factor cDNA into an expression vector;
  (d) expressing the recombinant Intrinsic Factor protein in a mammalian host cell system for a period of time and under conditions suitable for expression of the protein; and
  (e) purifying the Intrinsic Factor protein.

The recombinant porcine Intrinsic Factor produced in accordance with the method of this invention can be used in diagnostic assays to detect the levels of vitamin B12 in biological samples.

The Vitamin B12 Diagnostic Assay is part of the menu in platforms for diagnostic analyzers having such trademarks "IMx", "AxSYM" and "ARCHITECT", all of which are commercially available from Abbott Laboratories, Abbott Park, Ill. The intended use of the assay is for the quantitative determination of the vitamin B12 in human serum and plasma. The vitamin B12 assay for the "IMx" and "AXSYM" analyzers is based on the Microparticle Enzyme Immunoassay (MEIA) technology. The vitamin B12 assay for the "ARCHITECT" analyzer is a Chemiluminescent Microparticle Immunoassay (CMIA).

Intrinsic Factor is produced in the stomach. It binds to vitamin B12 in the proximal small intestine, thereby forming a complex with vitamin B12. This intact complex moves through the intestine until reaches the distal ileum, where it binds to high-affinity receptors, specific for Intrinsic Factor, located on the luminal surface of ileal absorptive cells (enterocytes). The Intrinsic Factor—vitamin B12 complex attaches to these surface receptors rapidly, enters these cells, and finally reaches the portal circulation. Thus, the Intrinsic Factor helps in the transport and absorption of vitamin B12 in the intestine. The ability of the Intrinsic Factor to specifically bind vitamin B12 is used as the premise in the diagnostic assays developed at Abbott Laboratories, Abbott Park, Ill. The level of vitamin B12 in a biological sample is determinative of how much vitamin B12 is bound to particles coated with Intrinsic Factor.

The percent identity between the nucleotide sequence of porcine Intrinsic Factor and human Intrinsic Factor is 83%. The percent identity between the nucleotide sequence of porcine Intrinsic Factor and mouse Intrinsic Factor is 79%. The percent identity between the nucleotide sequence of porcine Intrinsic Factor and rat Intrinsic Factor is 79%. The percent identity between the amino acid sequence of porcine Intrinsic Factor and human Intrinsic Factor is 81%. The percent identity between the amino acid sequence of porcine Intrinsic Factor and mouse Intrinsic Factor is 73%. The percent identity between the amino acid sequence of porcine Intrinsic Factor and rat Intrinsic Factor is 72%.

Production of the Recombinant Porcine Intrinsic Factor

Once the gene encoding the porcine Intrinsic Factor has been isolated, it may then be introduced into a mammalian host cell, preferably a Chinese Hamster Ovary (CHO) cell, through the use of a vector or construct. The vector, for example, a bacteriophage, cosmid or plasmid, may comprise the nucleotide sequence encoding the porcine Intrinsic Factor, as well as any regulatory sequence (e.g., promoter) which is functional in the host cell and is able to elicit expression of the porcine Intrinsic Factor encoded by the nucleotide sequence. The regulatory sequence (e.g., promoter) is in operable association with, or operably linked to, the nucleotide sequence. (A promoter is said to be "operably linked" with a coding sequence if the promoter affects transcription or expression of the coding sequence.) Suitable promoters include, for example, those from genes encoding alcohol dehydrogenase, glyceraldehyde-3-phosphate dehydrogenase, phosphoglucoisomerase, phosphoglycerate kinase, acid phosphatase, T7, TPI, lactase, metallothionein, cytomegalovirus immediate early, whey acidic protein, glucoamylase, and promoters activated in the presence of galactose, for example, GAL1 and GAL10. Additionally, nucleotide sequences which encode other proteins, oligosaccharides, lipids, etc. may also be included within the vector as well as other regulatory sequences such as a polyadenylation signal (e.g., the poly-A signal of SV-40T-antigen, ovalalbumin or bovine growth hormone). The choice of sequences present in the construct is dependent upon the desired expression products as well as the nature of the host cell.

As noted above, once the vector has been constructed, it may then be introduced into the host cell of choice (e.g., a mammalian cell) by methods known to those of ordinary skill in the art including, for example, transfection, transformation and electroporation (see *Molecular Cloning: A Laboratory Manual*, $2^{nd}$ ed., Vol. 1-3, ed. Sambrook et al., Cold Spring Harbor Laboratory Press (1989)). The host cell is then cultured under suitable conditions permitting expression of the genes leading to the production of the desired porcine Intrinsic Factor, which is then recovered and purified.

Expression in a host cell can be accomplished in a transient or stable fashion. Transient expression can occur from introduced constructs which contain expression signals functional in the host cell, but which constructs do not replicate and rarely integrate in the host cell, or when the host cell is not proliferating. Transient expression also can be accomplished by inducing the activity of a regulatable promoter operably linked to the gene of interest, although such inducible systems frequently exhibit a low basal level of expression. Stable expression can be achieved by introduction of a construct that can integrate into the host genome or that autonomously replicates in the host cell. Stable expression of the gene of interest can be selected through the use of a selectable marker located on or transfected with the expression construct, followed by selection for cells expressing the marker. When stable expression results from integration, the site of the construct's integration can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

To prepare an antibody of the invention, the antibody is raised against an antigen (i.e., the porcine Intrinsic Factor or fragment thereof) capable of eliciting production of the antibody. The present invention includes the isolated antibody or antibodies raised against the antigen, as well as antibody portions or fragments thereof. Further, the antibodies of the invention include monoclonal and recombinant antibodies, and portions or fragments thereof. In various embodiments, the antibody, or portion thereof, may comprise amino acid sequences derived entirely from a single species, such as a fully human or fully mouse antibody, or portion thereof. In other embodiments, the antibody, or portion thereof, may be a chimeric antibody or a CDR-grafted antibody (CDR, complementary determining region) or other form of humanized antibody.

The following non-limiting examples further illustrate this invention:

EXAMPLE I

Cloning of Porcine Intrinsic Factor into Eukaryotic Plasmid Vector

Intrinsic Factor (IF) is a glycoprotein 55-65 kDA in size that is produced by parietal cells in the stomach. Intrinsic Factor is necessary for the absorption of Vitamin B12 into the blood. Intrinsic Factor binds to free Vitamin B12 in the duodenum of the small intestine and transports Vitamin B12 to the ileum where it can be absorbed. The goal was to produce recombinant version of the porcine IF in an eukaryotic system using Chinese Hamster Ovary (CHO) cells.

Porcine Intrinsic Factor cDNA was produced using RT-PCR using total RNA extracted from porcine stomach tissues as the template and Forward primer huIF For 14 (SEQ ID No: 1) and reverse primer REV 1248 (SEQ ID No: 2). This resultant PCR product which is porcine Intrinsic Factor cDNA fragment, referred to herein as Porcine IF cDNA $_{14-1248}$, (1234 bp in length, denoted by SEQ ID 3, its reverse complement SEQ ID No. 4 and its amino acid sequence SEQ ID No. 5) (detailed in Patent Application 20060177872). This PCR fragment (Porcine IF cDNA $_{14-1248}$) was cloned into TA cloning vector pCR2.1 (purchased from Invitogen, Carlsbad, Calif.) into to create the plasmid pIF in pCR2.1-Clone #5 and then transformed into "TOP 10" *E. Coli* cells (from Invitogen, Carlsbad, Calif.). A PCR reaction was performed using plasmid (pIF in pCR2.1-Clone #5) as the template and primers pIF Sense-PCR1 and pIF Anti-Sense-PCR 1 (SEQ ID No. 6 and SEQ ID No. 7) to produce a PCR fragment 1264, referred to as Porcine IF cDNA $_{1264}$ (denoted by SEQ ID No. 8, its reverse complement SEQ ID No. 9 and its amino acid sequence SEQ ID No. 10). Another PCR was performed using the PCR product Porcine IF cDNA $_{1264}$ as the template, forward primer pIF Forward PCR3 (SEQ ID No. 11) and reverse primer pIF Reverse PCR3 (SEQ ID No. 12) to produce a PCR fragment 1298, referred to as Porcine IF cDNA$_{1298}$ denoted by SEQ ID No. 13, its reverse complement SEQ ID No. 14 and its amino acid sequence SEQ ID No. 15. This PCR product was digested with Hind III and Xho I and cloned into pcDNA3.1(+) vector. The resulting plasmid [called rIF-pcDNA3.1(+)] contains the Full-length Porcine IF cDNA, 1269 bp in length (referred to as Full-length Porcine IF cDNA $_{1269}$ with His-Tag and denoted by SEQ ID No. 16, its reverse complement by SEQ ID No.17, its amino acid sequence by SEQ ID No. 18) encoding 423 amino acids. The first 18 amino acids of this protein is the signal sequence (SEQ ID No: 19), the next 399 amino acid is the Mature Peptide [with cDNA sequence consisting of 1200 bp (SEQ ID: 20), its reverse complement is SEQ ID: 21 and amino acid sequence is SEQ ID No: 22] and the last 6 amino acids constitute the His-tag (SEQ ID 23).

This plasmid rIF-pcDNA3.1(+) was transformed into TOP 10 E. coli cells. Plasmid DNA from several transformants clones was sequenced. Upon sequence verification, clone #5 was chosen for further use.

It should be noted that isolation of the nucleic acid molecule of the present invention was quite surprising because initial attempts to obtain nucleic acid molecules using RT-PCR were unsuccessful. After numerous attempts, specific primers that were useful for isolating such nucleic acid molecules were discovered. The cDNA sequence of the porcine Intrinsic Factor that can be used to produce recombinant Intrinsic Factor protein is now known.

EXAMPLE II

Expression of Recombinant Porcine Intrinsic Factor in Chinese Hamster Ovary (CHO) Cells A Chinese Hamster Ovary (CHO) cell line that is adapted for suspension growth (CHO-S cells, Gibco Cat. No. 11619-012) was used for the transfection of the rIF-pcDNA3.1 (+) plasmid and stable expression of the full-length porcine Intrinsic Factor. The CHO-S cells were grown at 35° C. in a humidified incubator supplied with 5% $CO_2$. Cells were transfected with the rIF-pcDNA3.1(+) plasmid using the Invitrogen Lipofectamine 2000 Transfection Reagent Kit. Transfected cells were grown in a 6 well cell culture plate in CD CHO medium supplemented with 10 ml/L of HT Supplement, 8 mM L-Glutamine, 100 U penicillin, 100 ug streptomycin, and 2% FBS. Cells were then transferred into T75 cell culture flasks, and the FBS was removed from the medium for several passes.

The CHO-S cells transfected with the rIF-pcDNA3.1(+) plasmid were cloned by limiting dilution into CD CHO medium supplemented with 10 ml/L of HT Supplement, 8 mM L-Glutamine, 100 U penicillin, 100 ug streptomycin, and 1 mg/ml of Geneticin. Three 96-well plates were prepared. The first plate had an expected dilution of 3 cells/well, the second plate had an expected dilution of 0.3 cells/well, and the third plate had an expected dilution of 0.03 cells/well. The plates were incubated for 12 days at 35° C. in a humidified incubator with 5% CO2. As growth became apparent, 24 wells were chosen to be scaled up into a 24-well plate (20 wells were seeded from the 0.3 cells/well plate and 4 wells were seeded from the 0.03 cells/well plate). To the inventors' knowledge, this represents the first time functional porcine Intrinsic Factor was produced by expression in CHO cells.

EXAMPLE III

Figure 2:
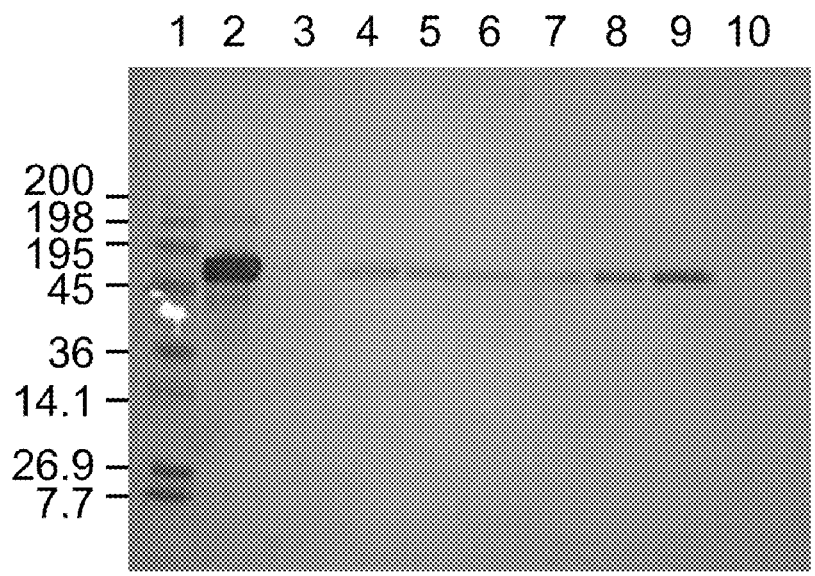
FIG. 2 illustrates another Western-blot that establishes the binding of recombinant porcine Intrinsic Factor (produced in CHO cells) to Vitamin B12. In particular, this figure illustrates two CHO cell clones that produced functional porcine Intrinsic Factor.

Demonstration of Binding of Recombinant Porcine Intrinsic Factor (rIF) Produced in CHO Cells to Anti-Intrinsic Factor Antibody using Western Blot Analysis Supernatants from all 24 wells were tested for rIF production using Western blot analysis that resulted in the selection of six clones for further analysis. The six clones were scaled up into T75 flasks and carried for several more passages. The supernatants for the six clones (Clone #4, #8, #10, #13, #17, #21) were tested for rIF production using Western blot analysis (FIG. 1) that resulted in the selection of two clones (Clone #13 and Clone #21) for further analysis (FIG. 2).

In the Western Blot Analysis referred to as "Conjugate blots, protein from various cell lines were run on a SDS-PAGE and blotted to Nitrocellulose membrane. These blots were then probed with Vitamin B-12 conjugated to Alkaline phospatase. The substrate was added to develop the color reaction. The protein bands that bind Vitamin B12 light up in the blot indicating that the protein is bound to the labeled Vitamin B12 (see FIGS. 1 and 2). In particular, the data presented in FIG. 1 and FIG. 2 demonstrate binding of recombinant porcine Intrinsic Factor (produced in CHO Cells) to Vitamin B12 and thus the functionality of the porcine Intrinsic Factor produced using CHO cells. The blots use labeled Vitamin-B12 instead of labeled antibodies. When the protein band lights up, this is an indication that the antibody is binding Vitamin B-12.

EXAMPLE IV

Feasibility of using Recombinant Porcine Intrinsic Factor in "ARCHITECT" Binding Capacity Assay for Vitamin B12

Both Clone #13 and #21 were split several times into CD CHO medium without Vitamin B12, 10 ml/L of HT Supplement, 8 mM L-Glutamine, 100 U penicillin, 100 ug streptomycin, and 1 mg/ml of Geneticin. Supernatants from both clones were testing via Western blot and on the ARCHITECT Binding Capacity Assay (FIG. 3). The ARCHITECT Binding Capacity Assay is a complementary assay. Therefore, the lower the results, the higher the binding capacity to vitamin B12. This resulted in the selection of Clone #21 (also referred to as C981-157-21).

The host cell line, designated C981-157-21 has been adapted for suspension tissue culture growth. Clone #21 (also referred to as C981-157-21) was sent to Bionique Testing Laboratories, Inc. (Saranac Lake, N.Y.) for mycoplasma testing. The results were negative for mycoplasma contamination. At passage 31, cells from the rIF C981-157-21 CHO-S clone were centrifuged, the pellet was resuspended in 50% conditioned medium, 50% fresh medium, and 7.5% DMSO and dispensed into appropriately labeled cryovials. The cells were stored at −70° C. for several days and transferred into liquid nitrogen for permanent storage.

EXAMPLE V

Purification of Recombinant Porcine Intrinsic Factor Secreted by CHO Cells

The CHO-S cell culture was grown at 20-liter scale using WAVE Technologies 20/50 System. Culture conditions were characterized and optimized for recombinant Intrinsic Factor production using Design of Experiments (DOE). A three-column purification process was developed and characterized to generate pure rIF. The process includes:

1) Nickel column purification: The recombinant porcine IF has a His-Tag at the C-terminus. This His-Tag is used in the affinity purification using a Nickel column.
2) $B_{12}$-Agarose column purification: Intrinsic Factor binds to Vitamin B12. This property is utilized in this second step of purification. The protein eluted from the nickel column is run through a Vitamin B12-agarose column where B12 is attached to agarose. Functionally active Intrinsic Factor binds to B12 in the column.
3) Concentration: The rIF eluted from this column is further concentrated at this step.
4) Gel Filtration column purification: The concentrated rIF from the $B_{12}$-Agarose column is run through a gel filtration column, which separates the proteins based on their molecular weight, to further purify rIF from other contaminants
5) Concentration: The rIF eluted from the Gel Filtration column is further concentrated at this step.

Purity and stability of rIF: The purity of rIF is consistently greater than 97% with high stability.

Protein Yield: Harvests from three 20-liter WAVE runs, after purification using the 3-column procedure yielded 29 to 43 mg of rIF at a minimum 99% purity.

EXAMPLE VI

ARCHITECT® B12 Assay

The ARCHITECT® B12 assay is a two-step assay with an automated sample pretreatment, for determining the presence of Vitamin B12 in human serum and plasma using Chemiluminescent Microparticle Immunoassay (CMIA) technology with flexible assay protocols. The ARCHITECT® analyzer and the method for using the ARCHITECT® analyzer are described in U.S. Pat. No. 5,795,784, the entirety of which is incorporated herein by reference. The assay for Vitamin B12 is described in ARCHITECT® System B12, List No. 6C09, 69-0689/R1, December 1998, Abbott Laboratories, Abbott Park, Ill., the entirety of which is incorporated herein by reference. The sample and Pre-Treatment Reagent 1, Pre-Treatment Reagent 2, and Pre-Treatment Reagent 3 are combined. An aliquot of the pre-treated sample is aspirated and transferred into a new reaction vessel. The pre-treated sample, assay diluent, and Intrinsic Factor coated paramagnetic microparticles are combined. Vitamin B12 present in the sample binds to the Intrinsic Factor coated microparticles. After washing, vitamin B12-acridinium-labeled conjugate is added in the second step. The vitamin B12-acridinium-labeled conjugate is capable of undergoing a chemiluminescent reaction. Pre-Trigger and Trigger solutions are then added to the reaction mixture; the resulting chemiluminescent reaction is measured as relative light units. An inverse relationship exists between the amount of vitamin B12 in the sample and the relative light units detected by the "ARCHITECT" i optical system. Further details on the system and assay technology can be found in "ARCHITECT" i System Operations Manual, the entirety of which is incorporated herein by reference.

The reagents for the assay are described below (the amounts per bottle are for 100 tests):

Intrinsic Factor coated Microparticles in borate buffer with protein (bovine) stabilizers. Preservative: antimicrobial agents. (1 bottle, 6.6 mL/bottle)

B12 acridinium-labeled Conjugate in MES buffer. Minimum concentration: 0.7 ng/mL. Preservative: antimicrobial agent. (1 bottle, 5.9 mL/bottle)

B12 Assay Diluent containing borate buffer with EDTA. Preservative: antimicrobial agents. (1 bottle, 10 mL/bottle)

B12 Pre-Treatment Reagent 1 containing 1.0 N sodium hydroxide with 0.005% potassium cyanide. (1 bottle, 27 mL/bottle)

B12 Pre-Treatment Reagent 2 containing alpha monothioglycerol and EDTA. (1 bottle, 5.5 mL/bottle)

B12 Pre-Treatment Reagent 3 containing cobinamide dicyanide in borate buffer with protein (avian) stabilizers. Preservative: Sodium Azide. (1 bottle, 5.5 mL/bottle)

"ARCHITECT" i Multi-Assay Manual Diluent containing phosphate buffered saline solution. Preservative: antimicrobial agent. (1 bottle, 100 mL/bottle)

"ARCHITECT" i Pre-Trigger Solution containing 1.32% (w/v) hydrogen peroxide.

"ARCHITECT" i Trigger Solution containing 0.35 N sodium hydroxide.

"ARCHITECT" i Wash Buffer containing phosphate buffered saline solution.

Preservative: antimicrobial agent.

FIG. 3 illustrates the binding data derived from the ARCHITECT assay. In particular, the assay was used to measure the binding capacity of the recombinant porcine Intrinsic Factor (produced in CHO Cells), in terms of light units. This is a complementary assay, so the lower the value, the better the binding capacity The nucleotide and amino acid sequences referred to in the specification are listed below:

LIST OF NUCLEOTIDE AND AMINO ACID SEQUENCE FOR
THE PORCINE INTRINSIC FACTOR cDNA CLONES

SEQ ID NO: 1 represents the nucleotide sequence of the Forward Primer huIF-For14 (29 nt).
(SEQ ID NO: 1)
5'-CCCTCTACCTCCTGAGCCTTCTCTGGGCT-3'

SEQ ID NO: 2 represents the nucleotide sequence of the Reverse Primer huIF 1248Rev (25 nt).
(SEQ ID NO: 2)
5'-CTGTGTGAAATTGGCTGTGATGTGC-3'

SEQ ID NO: 3 represents the nucleotide sequence of the Porcine IF cDNA$_{14-1248}$ (1234 bp).
(SEQ ID NO: 3)
5'-CCTCTACCTCCTGAGCCTTCTCTGGGCTGTGGCCGGAACCAGCACCC
AGACCCGAAGCTCATGCTCTGTTCCCTCTGCAGAGCAGCCCTTGGTTAAT
GGCATCCAGGTGCTCATGGAGCAGTCCGTGACCAGCTCGGCCTTCCCAAA
CCCCAGCATCCTGATTGCCATGAACCTGGCCGGAGCCTACAACACAGAGG
CCCAGGAGCTCCTGACTTACAAGCTCATGGCTACCAACACCTCCGACCTG
ACCACAGGTCAGCTCGCCCTCACCATCATGGCACTCACCTCCTCCTGCCG
AGACCCTGGGAACAGAATAGCCATTCTACAGGGGCAAATGGAGAACTGGG
CACCTCCAAGCCTTGATACCCATGCTTCAACCTTCTACGAGCCAAGTCTG
GGGATCCTGACGCTGTGCCAGAATAACCCGGAGAAGACCTTACCGCTAGC
AGCCCGTTTTGCCAAGACCCTGCTGGCCAATTCCTCTCCCTTCAACATGG
ACACAGGAGCAATGCAACCTTGGCCCTGACCTGTATGTACAACAAGATC
CCCGTAGGCTCAGAGGAAGGGTACAGAGCCCTGTTCAGTCAGGTACTGAG
GAATACTGTGGAGAATATCAGCATGAGGATCCAAGACAACGGAATCATTG
GAAACATCTATAGCACTGGCCTCGCCATGCAGGCTCTCTCTGTGACACCT
GAGCAACCTAACAAGGAGTGGGACTGCCAGAAGACCATGGATACTGTACT
TACTGAGATTAAGGAGGGGAAATTCCACAACCCCATGGCCATTGCCCAAA
TCCTCCCTTCCCTGAAAGGCAAGACCTATCTAGATGTGCCCCATGTGTCT
TGCAGCCCTGGTCATGAGGTGCCACCAACTCTACCCAACCACCCCAGCCC
TGTTCCCACCCCAGCACCCAACATCACCGTCATATACACCATAAATAACC
AGCTGAGGGGCGTGGAGCTGCTCTTCAATGAAACCATCAGTGTTAGTGTG
AAAAGAGGATCCGTGCTACTTATTGTCCTGGAGGAGGCACAGCGCAAAAA
CCCCAAGTTCAAATTTGAAACGACAATGACGTCCTGGGGACCGGTGGTCT

LIST OF NUCLEOTIDE AND AMINO ACID SEQUENCE FOR THE PORCINE INTRINSIC FACTOR cDNA CLONES

CTTCTATTAACAATATCGCTGAAAATGTCAACCACAGGACGTACTGGCAG
TTTCTGAGTGGCCAAACGCCCTTAAACGAAGGAGTTGCGGACTATATACC
CTTCAACCACGAGCACATCACAGCCAATTTCACACAG-3'

SEQ ID NO: 4 represents the reverse complement of the nucleotide sequence of Porcine IF cDNA$_{14-1248}$ (1234 bp).

(SEQ ID NO: 4)

5'-CTGTGTGAAATTGGCTGTGATGTGCTCGTGGTTGGGGTATATAGT
CCGCAACTCCTTCGTTTAAGGGCGTTTGGCCACTCAGAAACTGCCAGTAC
GTCCTGTGGTTGACATTTTCAGCGATATTGTTAATAGAAGAGACCACCGG
TCCCCAGGACGTCATTGTCGTTTCAAATTTGAACTTGGGGTTTTTGCGCT
GTGCCTCCTCCAGGACAATAAGTAGCACGGATCCTCTTTTCACACTAACA
CTGATGGTTTCATTGAAGAGCAGCTCCACGCCCCTCAGCTGGTTATTTAT
GGTGTATATGACGGTGATGTTGGGTGCTGGGGTGGGAACAGGGCTGGGGT
GGTTGGGTAGAGTTGGTGGCACCTCATGACCAGGGCTGCAAGACACATGG
GGCACATCTAGATAGGTCTTGCCTTTCAGGGAAGGGAGGATTTGGGCAAT
GGCCATGGGGTTGTGGAATTTCCCCTCCTTAATCTCAGTAAGTACAGTAT
CCATGGTCTTCTGGCAGTCCCACTCCTTGTTAGGTTGCTCAGGTGTCACA
GAGAGAGCCTGCATGGCGAGGCCAGTGCTATAGATGTTTCCAATGATTCC
GTTGTCTTGGATCCTCATGCTGATATTCTCCACAGTATTCCTCAGTACCT
GACTGAACAGGGCTCTGTACCCTTCCTCTGAGCCTACGGGGATCTTGTTG
TACATACAGGTCAGGGCCAAGGTTGCCATTGCTCCTGTGTCCATGTTGAA
GGGAGAGGAATTGGCCAGCAGGGTCTTGGCAAAACGGGCTGCTAGCGGTA
AGGTCTTCTCCGGGTTATTCTGGCACAGCGTCAGGATCCCCAGACTTGGC
TCGTAGAAGGTTGAAGCATGGATTCAAGGCTTGGAGGTGCCCAGTTCTC
CATTTGCCCCTGTAGAATGGCTATTCTGTTCCCAGGGTCTCGGCAGGAGG
AGGTGAGTGCCATGATGGTGAGGGCGAGCTGACCTGTGGTCAGGTCGGAG
GTGTTGGTAGCCATGAGCTTGTAAGTCAGGAGCTCCTGGGCCTCTGTGTT
GTAGGCTCCGGCCAGGTTCATGGCAATCAGGATGCTGGGGTTTGGGAAGG
CCGAGCTGGTCACGGACTGCTCCATGAGCACCTGGATGCCATTAACCAAG
GGCTGCTCTGCAGAGGGAACAGAGCATGAGCTTCGGGTCTGGGTGCTGGT
TCCGGCCACAGCCCAGAGAAGGCTCAGGAGGTAGAGG-3'

SEQ ID NO: 5 represents the amino acid sequence of the Porcine IF cDNA$_{14-1248}$ (411 aa).

(SEQ ID NO: 5)

LYLLSLLWAVAGTSTQTRSSCSVPSAEQPLVNGIQVLMEQSVTSSAFPNP
SILIAMNLAGAYNTEAQELLTYKLMATNTSDLTTGQLALTIMALTSSCRD
PGNRIAILQGQMENWAPPSLDTHASTFYEPSLGILTLCQNNPEKTLPLAA
RFAKTLLANSSPFNMDTGAMATLALTCMYNKIPVGSEEGYRALFSQVLRN
TVENISMRIQDNGIIGNIYSTGLAMQALSVTPEQPNKEWDCQKTMDTVLT
EIKEGKFHNPMAIAQILPSLKGKTYLDVPHVSCSPGHEVPPTLPNHPSPV
PTPAPNITVIYTINNQLRGVELLFNETISVSVKRGSVLLIVLEEAQRKNP
KFKFETTMTSWGPVVSSINNIAENVNHRTYWQFLSGQTPLNEGVADYYIP
FNHEHITANFTQ

SEQ ID NO: 6 represents the nucleotide sequence of the pIF Sense-PCR 1(36 nt).

(SEQ ID NO: 6)

5'-ATGGCCTGGTTTGCCCTCTACCTCCTGAGCCTTCTC-3'

SEQ ID NO: 7 represents the nucleotide sequence of the pIF Anti-Sense-PCR 1(38 nt).

(SEQ ID NO: 7)

5'-GATGGTGATGATGGTACTGTGTGAAATTGGCTGTGATG-3'

SEQ ID NO: 8 represents the nucleotide sequence of the Porcine IF cDNA$_{1264}$ (1264 bp).

(SEQ ID NO: 8)

5'-ATGGCCTGGTTTGCCCTCTACCTCCTGAGCCTTCTCTGGGCTGTGGC
CGGAACCAGCACCCAGACCCGAAGCTCATGCTCTGTTCCCTCTGCAGAGC
AGCCCTTGGTTAATGGCATCCAGGTGCTCATGGAGCAGTCCGTGACCAGC
TCGGCCTTCCCAAACCCCAGCATCCTGATTGCCATGAACCTGGCCGGAGC
CTACAACACAGAGGCCCAGGAGCTCCTGACTTACAAGCTCATGGCTACCA
ACACCTCCGACCTGACCACAGGTCAGCTCGCCCTCACCATCATGGCACTC
ACCTCCTCCTGCCGAGACCCTGGGAACAGAATAGCCATTCTACAGGGGCA
AATGGAGAACTGGGCACCTCCAAGCCTTGATACCATGCTTCAACCTTCT
ACGAGCCAAGTCTGGGGATCCTGACGCTGTGCCAGAATAACCCGGAGAAG
ACCTTACCGCTAGCAGCCCGTTTTGCCAAGACCCTGCTGGCCAATTCCTC
TCCCTTCAACATGGACACAGGAGCAATGGCAACCTTGGCCCTGACCTGTA
TGTACAACAAGATCCCCGTAGGCTCAGAGGAAGGGTACAGAGCCCTGTTC
AGTCAGGTACTGAGGAATACTGTGGAGAATATCAGCATGAGGATCCAAGA
CAACGGAATCATTGGAAACATCTATAGCACTGGCCTCGCCATGCAGGCTC
TCTCTGTGACACCTGAGCAACCTAACAAGGAGTGGGACTGCCAGAAGACC
ATGGATACTGTACTTACTGAGATTAAGGAGGGGAAATTCCACAACCCCAT
GGCCATTGCCCAAATCCTCCCTTCCCTGAAAGGCAAGACCTATCTAGATG

TGCCCCATGTGTCTTGCAGCCCTGGTCATGAGGTGCCACCAACTCTACCC
AACCACCCCAGCCCTGTTCCCACCCCAGCACCCAACATCACCGTCATATA
CACCATAAATAACCAGCTGAGGGGCGTGGAGCTGCTCTTCAATGAAACCA
TCAGTGTTAGTGTGAAAAGAGGATCCGTGCTACTTATTGTCCTGGAGGAG
GCACAGCGCAAAAACCCCAAGTTCAAATTTGAAACGACAATGACGTCCTG
GGGACCGGTGGTCTCTTCTATTAACAATATCGCTGAAAATGTCAACCACA
GGACGTACTGGCAGTTTCTGAGTGGCCAAACGCCCTTAAACGAAGGAGTT
GCGGACTATATACCCTTCAACCACGAGCACATCACAGCCAATTTCACACA
GTACCATCATCACCATC-3'

SEQ ID NO: 9 represents the reverse complement of the nucleotide sequence of Porcine IF cDNA$_{1264}$ (1264 bp).

(SEQ ID NO: 9)

5'-GATGGTGATGATGGTACTGTGTGAAATTGGCTGTGATGTGCTCGTGG
TTGAAGGGTATATAGTCCGCAACTCCTTCGTTTAAGGGCGTTTGGCCACT
CAGAAACTGCCAGTACGTCCTGTGGTTGACATTTTCAGCGATATTGTTAA
TAGAAGAGACCACCGGTCCCCAGGACGTCATTGTCGTTTCAAATTTGAAC
TTGGGGTTTTTGCGCTGTGCCTCCTCCAGGACAATAAGTAGCACGGATCC
TCTTTTCACACTAACACTGATGGTTTCATTGAAGAGCAGCTCCACGCCCC
TCAGCTGGTTATTTATGGTGTATATGACGGTGATGTTGGGTGCTGGGGTG
GGAACAGGGCTGGGGTGGTTGGGTAGAGTTGGTGGCACCTCATGACCAGG
GCTGCAAGACACATGGGGCACATCTAGATAGGTCTTGCCTTTCAGGGAAG
GGAGGATTTGGGCAATGGCCATGGGGTTGTGGAATTTCCCCTCCTTAATC
TCAGTAAGTACAGTATCCATGGTCTTCTGGCAGTCCCACTCCTTGTTAGG
TTGCTCAGGTGTCACAGAGAGAGCCTGCATGGCGAGGCCAGTGCTATAGA
TGTTTCCAATGATTCCGTTGTCTTGGATCCTCATGCTGATATTCTCCACA
GTATTCCTCAGTACCTGACTGAACAGGGCTCTGTACCCTTCCTCTGAGCC
TACGGGGATCTTGTTGTACATACAGGTCAGGGCCAAGGTTGCCATTGCTC
CTGTGTCCATGTTGAAGGGAGAGGAATTGGCCAGCAGGGTCTTGGCAAAA
CGGGCTGCTAGCGGTAAGGTCTTCTCCGGGTTATTCTGGCACAGCGTCAG
GATCCCCAGACTTGGCTCGTAGAAGGTTGAAGCATGGGTATCAAGGCTTG
GAGGTGCCCAGTTCTCCATTTGCCCCTGTAGAATGGCTATTCTGTTCCCA
GGGTCTCGGCAGGAGGAGGTGAGTGCCATGATGGTGAGGGCGAGCTGACC
TGTGGTCAGGTCGGAGGTGTTGGTAGCCATGAGCTTGTAAGTCAGGAGCT
CCTGGGCCTCTGTGTTGTAGGCTCCGGCCAGGTTCATGGCAATCAGGATG
CTGGGGTTTGGGAAGGCCGAGCTGGTCACGGACTGCTCCATGAGCACCTG
GATGCCATTAACCAAGGGCTGCTCTGCAGAGGGAACAGAGCATGAGCTTC
GGGTCTGGGTGCTGGTTCCGGCCACAGCCCAGAGAAGGCTCAGGAGGTAG
AGGGCAAACCAGGCCAT

SEQ ID NO: 10 represents the amino acid sequence of the Porcine IF cDNA$_{1264}$ (421 aa).

(SEQ ID NO: 10)

MAWFALYLLSLLWAVAGTSTQTRSSCSVPSAEQPLVNGIQVLMEQSVTSS
AFPNPSILIAMNLAGAYNTEAQELLTYKLMATNTSDLTTGQLALTIMALT
SSCRDPGNRIAILQGQMENWAPPSLDTHASTFYEPSLGILTLCQNNPEKT
LPLAARFAKTLLANSSPFNMDTGAMATLALTCMYNKIPVGSEEGYRALFS
QVLRNTVENISMRIQDNGIIGNIYSTGLAMQALSVTPEQPNKEWDCQKTM
DTVLTEIKEGKFHNPMAIAQILPSLKGKTYLDVPHVSCSPGHEVPPTLPN
HPSPVPTPAPNITVIYTINNQLRGVELLFNETISVSVKRGSVLLIVLEEA
QRKNPKFKFETTMTSWGPVVSSINNIAENVNHRTYWQFLSGQTPLNEGVA
DYIPFNHEHITANFTQYHHHH

SEQ ID NO: 11 represents the nucleotide sequence of the pIF Forward-PCR3 (36 nt).

(SEQ ID NO: 11)

5'-CGACTAAGCTTCCACCATGGCCTGGTTTGCCCTCTA-3'

SEQ ID NO: 12 represents the nucleotide sequence of the pIF Reverse PCR3 (41 nt).

(SEQ ID NO: 12)

5'-AATCCTCGAGTTAATGGTGATGGTGATGATGGTACTGTGTG-3'

SEQ ID NO: 13 represents the nucleotide sequence of the Porcine IF cDNA$_{1298}$ (1298 bp)

(SEQ ID NO: 13)

5'-CGACTAAGCTTCCACCATGGCCTGGTTTGCCCTCTACCTCCTGAGCC
TTCTCTGGGCTGTGGCCGGAACCAGCACCCAGACCCGAAGCTCATGCTCT
GTTCCCTCTGCAGAGCAGCCCTTGGTTAATGGCATCCAGGTGCTCATGGA
GCAGTCCGTGACCAGCTCGGCCTTCCCAAACCCCAGCATCCTGATTGCCA
TGAACCTGGCCGGACCTACAACACAGAGGCCCAGGAGCTCCTGACTTAC
AAGCTCATGGCTACCAACACCTCCGACCTGACCACAGGTCAGCTCGCCCT
CACCATCATGGCACTCACCTCCTCCTGCCGAGACCCTGGGAACAGAATAG
CCATTCTACAGGGGCAAATGGAGAACTGGGCACCTCCAAGCCTTGATACC
ATGCTTCAACCTTCTACGAGCCAAGTCTGGGGATCCTGACGCTGTGCCA
GAATAACCCGGAGAAGACCTTACCGCTAGCAGCCCGTTTTGCCAAGACCC

LIST OF NUCLEOTIDE AND AMINO ACID SEQUENCE FOR THE PORCINE INTRINSIC FACTOR cDNA CLONES

TGCTGGCCAATTCCTCTCCCTTCAACATGGACACAGGAGCAATGGCAACC
TTGGCCCTGACCTGTATGTACAACAAGATCCCCGTAGGCTCAGAGGAAGG
GTACAGAGCCCTGTTCAGTCAGGTACTGAGGAATACTGTGGAGAATATCA
GCATGAGGATCCAAGACAACGGAATCATTGGAAACATCTATAGCACTGGC
CTCGCCATGCAGGCTCTCTCTGTGACACCTGAGCAACCTAACAAGGAGTG
GGACTGCCAGAAGACCATGGATACTGTACTTACTGAGATTAAGGAGGGGA
AATTCCACAACCCCATGGCCATTGCCCAAATCCTCCCTTCCCTGAAAGGC
AAGACCTATCTAGATGTGCCCCATGTGTCTTGCAGCCCTGGTCATGAGGT
GCCACCAACTCTACCCAACCACCCCAGCCCTGTTCCCACCCCAGCACCCA
ACATCACCGTCATATACACCATAAATAACCAGCTGAGGGGCGTGGAGCTG
CTCTTCAATGAAACCATCAGTGTTAGTGTGAAAAGAGGATCCGTGCTACT
TATTGTCCTGGAGGAGGCACAGCGCAAAAACCCCAAGTTCAAATTTGAAA
CGACAATGACGTCCTGGGGACCGGTGGTCTCTTCTATTAACAATATCGCT
GAAAATGTCAACCACAGGACGTACTGGCAGTTTCTGAGTGGCCAAACGCC
CTTAAACGAAGGAGTTGCGGACTATATACCCTTCAACCACGAGCACATCA
CAGCCAATTTCACACAGTACCATCATCACCATCACCATTAACTCGAGGAT
T-3'

SEQ ID NO: 14 represents the reverse complement of the nucleotide sequence of Porcine IF cDNA₁₂₉₈ (1298 bp).

(SEQ ID NO: 14)
5'-AATCCTCGAGTTAATGGTGATGGTGATGATGGTACTGTGTGAAATTG
GCTGTGATGTGCTCGTGGTTGAAGGGTATATAGTCCGCAACTCCTTCGTT
TAAGGGCGTTTGGCCACTCAGAAACTGCCAGTACGTCCTGTGGTTGACAT
TTTCAGCGATATTGTTAATAGAAGAGACCACCGGTCCCCAGGACGTCATT
GTCGTTTCAAATTTGAACTTGGGGTTTTTGCGCTGTGCCTCCTCCAGGAC
AATAAGTAGCACGGATCCTCTTTTCACACTAACACTGATGGTTTCATTGA
AGAGCAGCTCCACGCCCCTCAGCTGGTTATTTATGGTGTATATGACGGTG
ATGTTGGGTGCTGGGGTGGGAACAGGGCTGGGGTGGTTGGGTAGAGTTGG
TGGCACCTCATGACCAGGGCTGCAAGACACATGGGGCACATCTAGATAGG
TCTTGCCTTTCAGGGAAGGGAGGATTTGGGCAATGGCCATGGGGTTGTGG
AATTTCCCCTCCTTAATCTCAGTAAGTACAGTATCCATGGTCTTCTGGCA
GTCCCACTCCTTGTTAGGTTGCTCAGGTGTCACAGAGAGAGCCTGCATGG
CGAGGCCAGTGCTATAGATGTTTCCAATGATTCCGTTGTCTTGGATCCTC
ATGCTGATATTCTCCACAGTATTCCTCAGTACCTGACTGAACAGGGCTCT
GTACCCTTCCTCTGAGCCTACGGGGATCTTGTTGTACATACAGGTCAGGG
CCAAGGTTGCCATTGCTCCTGTGTCCATGTTGAAGGGAGAGGAATTGGCC
AGCAGGGTCTTGGCAAAACGGGCTGCTAGCGGTAAGGTCTTCTCCGGGTT
ATTCTGGCACAGCGTCAGGATCCCCAGACTTGGCTCGTAGAAGGTTGAAG
CATGGGTATCAAGGCTTGGAGGTGCCCAGTTCTCCATTTGCCCCTGTAGA
ATGGCTATTCTGTTCCCAGGGTCTCGGCAGGAGGAGGTGAGTGCCATGAT
GGTGAGGCGAGCTGACCTGTGGTCAGGTCGGAGGTGTTGGTAGCCATGGA
GCTTGTAAGTCAGGAGCTCCTGGGCCTCTGTGTTGTAGGCTCCGGCCAGG
TTCATGGCAATCAGGATGCTGGGGTTTGGGAAGGCCGAGCTGGTCACGGA
CTGCTCCATGAGCACCTGGATGCCATTAACCAAGGGCTGCTCTGCAGAGG
GAACAGAGCATGAGCTTCGGGTCTGGGTGCTGGTTCCGGCCACAGCCCAG
AGAAGGCTCAGGAGGTAGAGGGCAAACCAGGCCATGGTGGAAGCTTAGTC
G-3'

SEQ ID NO: 15 represents the amino acid sequence of the Porcine IF cDNA₁₂₉₈ 423 aa).

(SEQ ID NO: 15)
MAWFALYLLSLLWAVAGTSTQTRSSCSVPSAEQPLVNGIQVLMEQSVTSS
AFPNPSILIAMNLAGAYNTEAQELLTYKLMATNTSDLTTGQLALTIMALT
SSCRDPGNRIAILQGQMENWAPPSLDTHASTFYEPSLGILTLCQNNPEKT
LPLAARFAKTLLANSSPFNMDTGAMATLALTCMYNKIPVGSEEGYRALFS
QVLRNTVENISMRIQDNGIIGNIYSTGLAMQALSVTPEQPNKEWDCQKTM
DTVLTEIKEGKFHNPMAIAQILPSLKGKTYLDVPHVSCSPGHEVPPTLPN
HPSPVPTPAPNITVIYTINNQLRGVELLFNETISVSVKRGSVLLEVLEEA
QRKNPKFKFETTMTSWGPVVSSINNIAENVNHRTYWQFLSGQTPLNEGVA
DYIPFNHEHITANFTQYHHHHHH

SEQ ID NO: 16 represents the nucleotide sequence of the Porcine IF cDNA₁₂₆₉ with His-Tag (1269 bp).

(SEQ ID NO: 16)
5'-ATGGCCTGGTTTGCCCTCTACCTCCTGAGCCTTCTGTGGGCTGTGGC
CGGAACCAGCACCCAGACCCGAAGCTCATGCTCTGTTCCCTCTGCAGAGC
AGCCCTTGGTTAATGGCATCCAGGTGCTCATGGAGCAGTCCGTGACCAGC
TCGGCCTTCCCAAACCCAGCATCCTGATTGCCATGAACCTGGCCGGAGC
CTACAACAGAGGCCCAGGACTCCTGACTTACAAGCTCATGGCTACCAACAC
ACACCTCCGACCTGACCACAGGTCAGCTCGCCCTCACCATCATGGCACTC
ACCTCCTCCTGCCGAGACCCTGGGAACAGAATAGCCATTCTACAGGGGCA
AATGGAGAACTGGGCACCTCCAAGCCTTGATACCCATGCTTCAACCTTCT
ACGAGCCAAGTCTGGGGATCCTGACGCTGTGCCAGAATAACCCGGAGAAG
ACCTTACCGCTAGCAGCCCGTTTTGCCAAGACCCTGCTGGCCAATTCCTC

TCCCTTCAACATGGACACAGGAGCAATGGCAACCTTGGCCCTGACCTGTA
TGTACAACAAGATCCCCGTAGGCTCAGAGGAAGGGTACAGAGCCCTGTTC
AGTCAGGTACTGAGGAATACTGTGGAGAATATCAGCATGAGGATCCAAGA
CAACGGAATCATTGGAAACATCTATAGCACTGGCCTCGCCATGCAGGCTC
TCTCTGTGACACCTGAGCAACCTAACAAGGAGTGGGACTGCCAGAAGACC
ATGGATACTGTACTTACTGAGATTAAGGAGGGGAAATTCCACAACCCCAT
GGCCATTGCCCAAATCCTCCCTTCCCTGAAAGGCAAGACCTATCTAGATG
TGCCCCATGTGTCTTGCAGCCCTGGTCATGAGGTGCCACCAACTCTACCC
AACCACCCCAGCCCTGTTCCCACCCCAGCACCCAACATCACCGTCATATA
CACCATAAATAACCAGCTGAGGGGCGTGGAGCTGCTCTTCAATGAAACCA
TCAGTGTTAGTGTGAAAAGAGGATCCGTGCTACTTATTGTCCTGGAGGAG
GCACAGCGCAAAAACCCCAAGTTCAAATTTGAAACGACAATGACGTCCTG
GGGACCGGTGGTCTCTTCTATTAACAATATCGCTGAAAATGTCAACCACA
GGACGTACTGGCAGTTTCTGAGTGGCCAAACGCCCTTAAACGAAGGAGTT
GCGGACTATATACCCTTCAACCACGAGCACATCACAGCCAATTTCACACA
GTACCATCATCACCATCACCATTAACTCGAGGATT-3'

SEQ ID NO: 17 represents the reverse complement of the nucleotide sequence of Porcine IF cDNA₁₂₆₉ with His-Tag (1269 bp).

(SEQ ID NO: 17)
5'-ATGGTGATGGTGATGATGGTACTGTGTGAAATTGGCTGTGATGTGCT
CGTGGTTGAAGGGTATATAGTCCGCAACTCCTTCGTTTAAGGGCGTTTGG
CCACTCAGAAACTGCCAGTACGTCCTGTGGTTGACATTTTCAGCGATATT
GTTAATAGAAGAGACCACCGGTCCCCAGGACGTCATTGTCGTTTCAAATT
TGAACTTGGGGTTTTTGCGCTGTGCCTCCTCCAGGACAATAAGTAGCACG
GATCCTCTTTTCACACTAACACTGATGGTTTCATTGAAGAGCAGCTCCAC
GCCCCTCAGCTGGTTATTTATGGTGTATATGACGGTGATGTTGGGTGCTG
GGGTGGGAACAGGGCTGGGGTGGTTGGGTAGAGTTGGTGGCACCTCATGA
CCAGGGCTGCAAGACACATGGGGCACATCTAGATAGGTCTTGCCTTTCAG
GGAAGGGAGGATTTGGGCAATGGCCATGGGGTTGTGGAATTTCCCCTCCT
TAATCTCAGTAAGTACAGTATCCATGGTCTTCTGGCAGTCCCACTCCTTG
TTAGGTTGCTCAGGTGTCACAGAGAGAGCCTGCATGGCGAGGCCAGTGCT
ATAGATGTTTCCAATGATTCCGTTGTCTTGGATCCTCATGCTGATATTCT
CCACAGTATTCCTCAGTACCTGACTGAACAGGGCTCTGTACCCTTCCTCT
GAGCCTACGGGGATCTTGTTGTACATACAGGTCAGGGCCAAGGTTGCCAT
TGCTCCTGTGTCCATGTTGAAGGGAGAGGAATTGGCCAGCAGGGTCTTGG
CAAAACGGGCTGCTAGCGGTAAGGTCTTCTCCGGGTTATTCTGGCACAGC
GTCAGGATCCCCAGACTTGGCTCGTAGAAGGTTGAAGCATGGGTATCAAG
GCTTGGAGGTGCCCAGTTCTCCATTTGCCCCTGTAGAATGGCTATTCTGT
TCCCAGGGTCTCGGCAGGAGGAGGTGAGTGCCATGATGGTGAGGCGAGC
TGACCTGTGGTCAGGTCGGAGGTGTTGGTAGCCATGAGCTTGTAAGTCAG
GAGCTCCTGGGCCTCTGTGTTGTAGGCTCCGGCCAGGTTCATGGCAATCA
GGATGCTGGGGTTTGGGAAGGCCGAGCTGGTCACGGACTGCTCCATGAGC
ACCTGGATGCCATTAACCAAGGGCTGCTCTGCAGAGGGAACAGAGCATGA
GCTTCGGGTCTGGGTGCTGGTTCCGGCCACAGCCCAGAGAAGGCTCAGGA
GGTAGAGGGCAAACCAGGCCAT

SEQ ID NO: 18 represents the amino acid sequence of the Porcine IF cDNA₁₂₆₉ with His-Tag (423 aa).

(SEQ ID NO: 18)
MAWFALYLLSLLWAVAGTSTQTRSSCSVPSAEQPLVNGIQVLMEQSVTSS
AFPNPSILIAMNLAGAYNTEAQELLTYKLMATNTSDLTTGQLALTIMALT
SSCRDPGNRIAILQGQMENWAPPSLDTHASTFYEPSLGILTLCQNNPEKT
LPLAARFAKTLLANSSPFNMDTGAMATLALTCMYNKIPVGSEEGYRALFS
QVLRNTVENISMRIQDNGIIGNIYSTGLAMQALSVTPEQPNKEWDCQKTM
DTVLTEIKEGKFHNPMAIAQILPSLKGKTYLDVPHVSCSPGHEVPPTLPN
HPSPVPTPAPNITVIYTINNQLRGVELLFNETISVSVKRGSVLLIVLEEA
QRKNPKFKFETTMTSWGPVVSSINNIAENVNHRTYWQFLSGQTPLNEGVA
DYIPFNHEHITANFTQYHHHHHH

SEQ ID NO: 19 represents the amino acid sequence of the Porcine IF Signal Sequence (18 aa).

(SEQ ID NO: 19)
MAWFALYLLSLLWAVAGT

SEQ ID NO: 20 represents the nucleotide sequence of the Porcine IF cDNA Mature Peptide (1200 bp).

(SEQ ID NO: 20)
5'-AGCACCCAGACCCGAAGCTCATGCTCTGTTCCCTCTGCAGAGCAGCC
CTTGGTTAATGGCATCCAGGTGCTCATGGAGCAGTCCGTGACCAGCTCGG
CCTTCCCAAACCCAGCATCCTGATTGCCATGAACCTGGCCGGAGCCTAC
AACACAGAGGCCCAGGAGCTCCTGACTTACAAGCTCATGGCTACCAACAC
CTCCGACCTGACCACAGGTCAGCTCGCCCTCACCATCATGGCACTCACCT
CCTCCTGCCGAGACCCTGGGAACAGAATAGCCATTCTACAGGGGCAAATG
GAGAACTGGGCACCTCCAAGCCTTGATACCCATGCTTCAACCTTCTACGA
GCCAAGTCTGGGGATCCTGACGCTGTGCCAGAATAACCCGGAGAAGACCT

LIST OF NUCLEOTIDE AND AMINO ACID SEQUENCE FOR THE PORCINE INTRINSIC FACTOR cDNA CLONES

```
TACCGCTAGCAGCCCGTTTTGCCAAGACCCTGCTGGCCAATTCCTCTCCC
TTCAACATGGACACAGGAGCAATGGCAACCTTGGCCCTGACCTGTATGTA
CAACAAGATCCCCGTAGGCTCAGAGGAAGGGTACAGAGCCCTGTTCAGTC
AGGTACTGAGGAATACTGTGGAGAATATCAGCATGAGGATCCAAGACAAC
GGAATCATTGGAAACATCTATAGCACTGGCCTCGCCATGCAGGCTCTCTC
TGTGACACCTGAGCAACCTAACAAGGAGTGGGACTGCCAGAAGGACCATGG
ATACTGTACTTACTGAGATTAAGGAGGGGAAATTCCACAACCCCATGGCC
ATTGCCCAAATCCTCCCTTCCCTGAAAGGCAAGACCTATCTAGATGTGCC
CCATGTGTCTTGCAGCCCTGGTCATGAGGTGCCACCAACTCTACCCAACC
ACCCCAGCCCTGTTCCCACCCCAGCACCCAACATCACCGTCATATACACT
ATAAATAACCAGCTGAGGGGCGTGGAGCTGCTCTTCAATGAAACCATCAG
TGTTAGTGTGAAAAGAGGATCCGTGCTACTTATTGTCCTGGAGGAGGCAC
AGCGCAAAAACCCCAAGTTCAAATTTGAAACGACAATGACGTCCTGGGGA
CCGGTGGTCTCTTCTATTAACAATATCGCTGAAAATGTCAACCACAGGAC
GTACTGGCAGTTTCTGAGTGGCCAAACGCCCTTAAACGAAGGAGTTGCGG
ACTATATACCCTTCAACCACGAGCACATCACAGCCAATTTCACACAGTAC
TAA-3'
```

SEQ ID NO: 21 represents the reverse complement of the nucleotide sequence of the Porcine IF cDNA Mature Peptide (1200 bp).

(SEQ ID NO: 21)
```
5'-TTAGTACTGTGTGAAATTGGCTGTGATGTGCTCGTGGTTGAAGGGTA
TATAGTCCGCAACTCCTTCGTTTAAGGGCGTTTGGCCACTCAGAAACTGC
CAGTACGTCCTGTGGTTGACATTTTCAGCGATATTGTTAATAGAAGAGAC
CACCGGTCCCCAGGACGTCATTGTCGTTTCAAATTTGAACTTGGGGTTTT
TGCGCTGTGCCTCCTCCAGGACAATAAGTAGCACGGATCCTCTTTTCACA
CTAACACTGATGGTTTCATTGAAGAGCAGCTCCACGCCCCTCAGCTGGTT
ATTTATGGTGTATATGACGGTGATGTTGGGTGCTGGGGTGGGAACAGGGC
TGGGGTGGTTGGGTAGAGTTGGTGGCACCTCATGACCAGGGCTGCAAGAC
ACATGGGGCACATCTAGATAGGTCTTGCCTTTCAGGGAAGGGAGGATTTG
GGCAATGGCCATGGGGTTGTGGAATTTCCCCTCCTTAATCTCAGTAAGTA
CAGTATCCATGGTCTTCTGGCAGTCCCACTCCTTGTTAGGTTGCTCAGGT
GTCACAGAGAGCCTGCATGGCGAGGCCAGTGCTATAGATGTTTCCAAT
GATTCCGTTGTCTTGGATCCTCATGCTGATATTCTCCACAGTATTCCTCA
GTACCTGACTGAACAGGGCTCTGTACCCTTCCTCTGAGCCTACGGGGATC
```

LIST OF NUCLEOTIDE AND AMINO ACID SEQUENCE FOR THE PORCINE INTRINSIC FACTOR cDNA CLONES

```
TTGTTGTACATACAGGTCAGGGCCAAGGTTGCCATTGCTCCTGTGTCCAT
GTTGAAGGGAGAGGAATTGGCCAGCAGGGTCTTGGCAAAACGGGCTGCTA
GCGGTAAGGTCTTCTCCGGGTTATTCTGGCACAGCGTCAGGATCCCCAGA
CTTGGCTCGTAGAAGGTTGAAGCATGGGTATCAAGGCTTGGAGGTGCCCA
GTTCTCCATTTGCCCCTGTAGAATGGCTATTCTGTTCCCAGGGTCTCGGC
AGGAGGAGGTGAGTGCCATGATGGTGAGGGCGAGCTGACCTGTGGTCAGG
TCGGAGGTGTTGGTAGCCATGAGCTTGTAAGTCAGGAGCTCCTGGGCCTC
TGTGTTGTAGGCTCCGGCCAGGTTCATGGCAATCAGGATGCTGGGGTTTG
GGAAGGCCGAGCTGGTCACGGACTGCTCCATGAGCACCTGGATGCCATTA
ACCAAGGGCTGCTCTGCAGAGGGAACAGAGCATGAGCTTCGGGTCTGGGT
GCT-3'
```

SEQ ID NO: 22 represents the amino acid sequence of the Porcine IF Mature Peptide (399 aa).

(SEQ ID NO: 22)
```
STQTRSSCSVPSAEQPLVNGIQVLMEQSVTSSAFPNPSILIAMNLAGAYN
TEAQELLTYKLMATNTSDLTTGQLALTIMALTSSCRDPGNRIAILQGQME
NWAPPSLDTHASTFYEPSLGILTLCQNNPEKTLPLAARFAKTLLANSSPF
NMDTGAMATLALTCMYNKIPVGSEEGYRALFSQVLRNTVENISMRIQDNG
IIGNIYSTGLAMQALSVTPEQPNKEWDCQKTMDTVLTEIKEGKFHNPMAI
AQILPSLKGKTYLDVPHVSCSPGHEVPPTLPNHPSPVPTPAPNITVIYTI
NNQLRGVELLFNETISVSVKRGSVLLIVLEEAQRKNPKFKFETTMTSWGP
VVSSINNIAENVNHRTYWQFLSGQTPLNEGVADYIPFNHEHITANFTQY
```

SEQ ID NO: 23 represents the amino acid sequence of the His-Tag (6 aa).

(SEQ ID NO: 23)
HHHHHH

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method of producing functional porcine Intrinsic Factor which binds to Vitamin B12 in an assay comprising the steps of:
   (a) isolating a nucleic acid sequence comprising or complementary to a nucleotide sequence:
   i) encoding porcine Intrinsic Factor comprising an amino acid sequence having at least 85% identity to SEQ ID NO: 22;
   (b) constructing a vector comprising: i) said isolated nucleic acid sequence operably linked to ii) a regulatory sequence; and
   (c) introducing said vector into a host cell for a time and under conditions sufficient for expression of said functional porcine Intrinsic Factor, wherein said host cell is a mammalian cell, and said mammalian cell is a Chinese Hamster Ovary (CHO) cell.

2. The method of claim 1, wherein said regulatory sequence is a promoter.

3. The method of claim 1, wherein said amino acid sequence has at least 90% identity to SEQ ID NO: 22.

4. The method of claim 3, wherein said amino acid sequence is SEQ ID NO: 22.

5. A method of producing recombinant porcine Intrinsic Factor having at least 97% purity comprising the steps of:
   (a) isolating a nucleic acid sequence comprising or complementary to a nucleotide sequence:
   i) encoding porcine Intrinsic Factor comprising an amino acid sequence having at least 85% identity to SEQ ID NO: 22;
   (b) constructing a vector comprising: i) said isolated nucleotide sequence operably linked to ii) a regulatory sequence; and
   (c) introducing said vector into a host cell for a time and under conditions sufficient for expression of said porcine Intrinsic Factor, wherein said host cell is a mammalian cell, wherein said mammalian cell is a Chinese Hamster Ovary cell;
(d) subjecting said expressed porcine Intrinsic Factor to a first affinity chromatography procedure;
(e) subjecting resulting porcine Intrinsic Factor of step (d) to a second affinity chromatography procedure; and
(f) subjecting resulting porcine Intrinsic Factor of step (e) to a size exclusion chromatography procedure wherein resulting porcine Intrinsic Factor has a purity of at least 97%.

6. The method of claim 5, wherein said first affinity chromatography procedure comprises use of a nickel column.

7. The method of claim 6, wherein said second affinity chromatography procedure comprises use of a Vitamin B12 column.

8. The method of claim 7, wherein said purity of said porcine intrinsic factor is 99%.

* * * * *